US00RE35593E

United States Patent [19]

Orlek et al.

[11] E Patent Number: Re. 35,593

[45] Reissued Date of Patent: Aug. 19, 1997

[54] AZABICYLO OXIME COMPOUNDS

[75] Inventors: Barry S. Orlek; Steven M. Bromidge; Steven Dabbs, all of Harlow, England

[73] Assignee: Beecham Group p.l.c., Brentwood

[21] Appl. No.: 585,113

[22] Filed: Jan. 11, 1996

Related U.S. Patent Documents

Reissue of:

[64] Patent No.: 5,278,170
Issued: Jan. 11, 1994
Appl. No.: 785,884
Filed: Oct. 30, 1991

U.S. Applications:

[63] Continuation of Ser. No. 508,100, Apr. 11, 1990, abandoned.

[30] Foreign Application Priority Data

Apr. 13, 1989 [GB] United Kingdom ..... 8908365
Oct. 16, 1989 [GB] United Kingdom ..... 8923299

[51] Int. Cl.[6] ..... C07D 471/08; C07D 453/02; A61K 31/435; A61K 31/42

[52] U.S. Cl. ..... 514/304; 514/305; 514/413; 546/124; 546/133; 548/453

[58] Field of Search ..... 514/304, 305, 514/413; 546/124, 133; 548/453

[56] References Cited

U.S. PATENT DOCUMENTS

| | | | |
|---|---|---|---|
| 4,546,185 | 10/1985 | Bondlou et al. | 546/133 |
| 4,710,508 | 12/1987 | Bergmeier et al. | 546/357 |
| 4,927,837 | 5/1990 | Galliani et al. . | |
| 4,937,239 | 6/1990 | Lauffer et al. | 514/183 |
| 5,015,655 | 5/1991 | Galliani et al. | 514/413 |
| 5,110,828 | 5/1992 | Bromidge et al. | 546/133 |
| 5,132,316 | 7/1992 | Hadley et al. | 548/453 X |
| 5,217,975 | 6/1993 | Wadworth et al. | 514/305 |

FOREIGN PATENT DOCUMENTS

| | | |
|---|---|---|
| 0094742 | 11/1983 | European Pat. Off. . |
| 239445 | 9/1987 | European Pat. Off. . |
| 0261763 | 3/1988 | European Pat. Off. . |
| 0257741 | 3/1988 | European Pat. Off. . |
| 271798 | 6/1988 | European Pat. Off. . |
| 0287356 | 10/1988 | European Pat. Off. . |
| 288394 | 10/1988 | European Pat. Off. . |
| 0291673 | 11/1988 | European Pat. Off. . |
| 308283 | 3/1989 | European Pat. Off. . |
| 308284 | 3/1989 | European Pat. Off. . |
| 0338723 | 10/1989 | European Pat. Off. . |
| 0316713 | 12/1989 | European Pat. Off. . |

*Primary Examiner*—Fiona Powers
*Attorney, Agent, or Firm*—Hopgood, Calimafde, Kalil & Judlowe

[57] ABSTRACT

A compound of formula (I) or a pharmaceutically acceptable salt thereof:

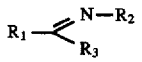

(I)

wherein $R^1$ represents

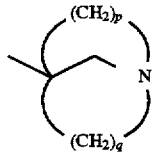

(A)

or

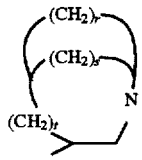

(B)

in which each of p and q independently represents an integer of 2 to 4, r represents an integer of 2 to 4, s represents 1 or 2 and t represents 0 or 1;

$R_2$ is a group $OR_4$, where $R_4$ is $C_{1-4}$ alkyl, $C_{2-4}$ alkenyl, $C_{2-4}$ alkynyl, a group $OCOR_5$ where $R_5$ is hydrogen or $R_4$, or a group $NHR_6$ or $NR_7R_8$ where $R_6$, $R_7$ and $R_8$ are independently $C_{1-2}$ alkyl; and $R_3$ is chloro, fluoro, bromo, cyclopropyl, $C_{1-3}$ alkyl substituted by one, two or three halogen atoms, or $R_3$ is a group $(CH_2)_nR_9$ where $R_9$ is —CN, —OH, —$OCH_3$, —SH, —$SCH_3$, —C≡CH or —CH=$CH_2$ and n is O or 1, with the proviso that when n is 0, $R_9$ is not —OH or —SH.

14 Claims, No Drawings

AZABICYLO OXIME COMPOUNDS

Matter enclosed in heavy brackets [ ] appears in the original patent but forms no part of this reissue specification; matter printed in italics indicates the additions made by reissue.

This application is a continuation of application Ser. No. 508,100, filed Apr. 11, 1990, now abandoned.

This invention relates to compounds having pharmaceutical activity, to a process for their preparation and their use as pharmaceuticals.

EP-A-0257741 and EP-A No. 0338723 (Beecham Group p.l.c.) disclose certain azabicyclic compounds which enhance acetylcholine function via an action at muscarinic receptors within the central nervous system. EP-A-0316718 (Ferrosan) discloses certain azabicyclic muscarinic cholinergic compounds.

A novel group of compounds has now been discovered which also enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

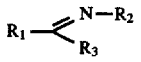

(I)

wherein $R_1$ represents

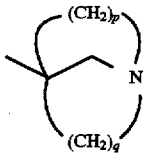

(A)

or

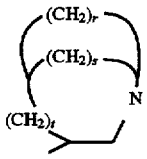

(B)

in which each of p and q independently represents an integer of 2 to 4, r represents an integer of 2 to 4, s represents 1 or 2 and t represents 0 or 1;

$R_2$ is a group $OR_4$, where $R_4$ is $C_{1-4}$ alkyl, $C_{2-4}$ alkenyl, $C_{2-4}$ alkynyl, a group $OCOR_5$ where $R_5$ is hydrogen or $R_4$, or a group $NHR_6$ or $NR_7R_8$ where $R_6$, $R_7$ and $R_8$ are independently $C_{1-2}$ alkyl; and $R_3$ is chloro, fluoro, bromo, cyclopropyl, $C_{1-3}$ alkyl substituted by one, two or three halogen atoms, or $R_3$ is a group $(CH_2)_nR_9$ where $R_9$ is —CN, —OH, —$OCH_3$, —SH, —$SCH_3$, —C≡CH or —CH=$CH_2$ and n is O or 1, with the proviso that when n is O, $R_9$ is not —OH or —SH.

The term halogen includes bromine, chlorine, fluorine and iodine, preferably fluorine.

Compounds of formula (I) are capable of existing in a number of stereoisomeric forms including geometric isomers such as syn and anti and, for certain compounds, enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

Compounds of formula (I) having two assymetric centres which have the stereochemical configuration in which the group —$C(R_3)$=$NR_2$ and the $(CH_2)_s$ bridge are on the same side of the plane of the molecule which contains both bridgehead atoms and the ring carbon atom bonded to the aforesaid group will hereinafter be referred to as having the exo configuration.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

The term pharmaceutically acceptable salt encompasses solvates and hydrates. Thus where compounds of formula (I) or pharmaceutically acceptable salts thereof form solvates or hydrates, these also form an aspect of the invention.

Preferably, p and q each independently represents 2 or 3. Most preferably p represents 2 and q represents 2 or 3.

Preferred combinations of (r,s,t) include (2,2,0), (2,1,1), (3,1,1), (2,1,0) and (3,1,0), most preferably (2,2,0).

The groups $R_4$ and $R_5$ in $R_2$ are preferably selected from methyl, ethyl, allyl and propargyl. $R_6$, $R_7$ and $R_8$ are preferably methyl. Suitable values for $R_2$ include methoxy, ethoxy, allyloxy, propargyloxy, acetoxy and dimethylamino, preferably methoxy.

Suitable examples for $R_3$ include cyclopropyl, chloro, fluoro and bromo and when $R_3$ is a group $(CH_2)_nR_9$ and n is O, suitable examples of $R_9$ include —CN, —$OCH_3$ or —C≡CH, preferably CN. When n is 1, an example of $R_9$ is CN.

The invention also provides a process for the preparation of a compound of formula (I), or a pharmaceutically acceptable salt thereof, which process comprises:

(a) reacting a compound of formula (II):

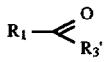

(II)

with a compound of formula (III):

$R_2$—$NH_2$ (III)

wherein $R_2'$ represents $R_2$ or hydroxy, and $R_3'$ represents $R_3$ or a group convertible thereto, converting $R_2'$ to $R_2$ when hydroxy, converting $R_3'$ when other than $R_3$ to $R_3$, wherein $R_1$, $R_2$ and $R_3$ are as defined in formula (I), and thereafter optionally forming a pharmaceutically acceptable salt;

(b) reacting a compound of formula (IV):

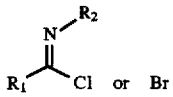

(IV)

with a compound of formula (V):

M—$R_3'$ (V)

capable of generating an $R_3'$ nucleophile wherein $R_3'$ represents $R_3$ or a group convertible thereto, converting $R_3'$ when other than $R_3$ to $R_3$, wherein $R_1$, $R_2$ and $R_3$ are as defined in formula (I), and thereafter optionally forming a pharmaceutically acceptable salt; or (c) reacting a compound of formula (IVa)

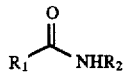

(IVa)

wherein $R_1$ and $R_2$ are as defined in formula (I), with a chlorinating, brominating or fluorinating agent, optionally converting $R_3$ when chloro or bromo to other $R_3$, and thereafter optionally forming a pharmaceutically acceptable salt.

It will be appreciated that compounds of formula (IV) are identical to compounds of formula (I) in which $R_3$ is chloro or bromo, and as such are themselves part of the invention.

The reaction between the compounds of formulae (II) and (III) is preferably carried out in a hydroxylic solvent such as methanol or ethanol, at ambient temperature, or where appropriate, at elevated temperature.

Where $R_2$ in compounds of formula (I) is a group $OR_4$, $NHR_6$ or $NR_7R_8$, a compound of formula (II) is conveniently reacted with a compound of formula (III) in which $R_2'$ is $R_2$.

Where $R_2$ in compounds of formula (I) is a group $OCOR_5$, a compound of formula (II) may be reacted with the compound of formula (III) in which $R_2'$ is hydroxy, with subsequent acylation of the resulting oxime by treatment with a suitable acylating agent such as an acyl halide, for example acetyl chloride.

The reaction between compounds of formulae (IV) and (V) may be carried out under standard conditions for the displacement of halogen by a nucleophile.

Where $R_3$ in compounds of formula (I) is fluoro, the residue M is suitably caesium, the caesium fluoride reagent being supported on calcium fluoride in dimethylformamide at elevated temperature for a prolonged period. This route for introduction of $R_3$ fluoro is preferred where $R_1$ represents group (B).

Where $R_3$ in compounds of formula (I) is a group $(CH_2)_nR_9$ and n is O, the residue M is suitably an alkali metal such as sodium or lithium. Where, for example, $R_9$ is —CN or —$OCH_3$, the reaction is conveniently carried out at elevated temperature in an inert solvent such as dimethylsulphoxide or methanol.

Where $R_3$ in compounds of formula (I) is a group $(CH_2)_n R_9$ and n is 1, the compound of formula (V) is suitably an organolithium or Grignard reagent. The reaction may be carried out using conditions generally used for reactions with Grignard reagents, for example using anhydrous reagents under an inert atmosphere and at reduced temperature.

The product of the reaction of compounds of formulae (II) and (III) and formulae (IV) and (V) is a compound of formula (IIa):

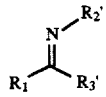

(IIa)

wherein $R_2'$ represents $R_2$ or hydroxy and $R_3'$ represents $R_3$ or a group convertible thereto, and $R_1$, $R_2$ and $R_3$ are as defined in formula (I).

Intermediates of formula (IIa) wherein $R_2'$ is not $R_2$ when $R_3'$ is $R_3$, also form part of the invention.

It will be appreciated that the reaction of compounds of formula (IVa) with a chlorinating, brominating or fluorinating agent will yield compounds of formula (I) wherein $R_3$ is chloro, bromo or fluoro. Suitable chlorinating agents include phosphorus pentachloride which undergoes reaction in nitromethane at reduced temperature, for example 0° C., and dichlorotriphenylphosphine (carbon tetrachloride/triphenyl phosphine) which undergoes reaction in acetonitrile at elevated temperature, for example at the boiling point of the solvent. Suitable brominating agents include dibromotriphenylphosphine (carbon tetrabromide/triphenylphosphine) which undergoes reaction in acetonitrile at elevated temperature, for example at the boiling point of the solvent. Suitable fluorinating agents include diethylaminosulphur trifluoride (DAST) which also undergoes reaction in acetonitrile at elevated temperature.

Conversion of the resulting $R_3$ halogen group when chloro or bromo to other $R_3$ groups may be effected by reaction variant (b) above.

Compounds of formula (II) and compounds of formulae (IV) and (IVa) may be prepared from an intermediate compound of formula (VI):

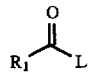

(VI)

in which L is a leaving group such as chloro, bromo or $C_{1-4}$ alkoxy and $R_1$ is as defined in formula (I). A compound of formula (VI) in which L is preferably chloro or bromo may be reacted with N,O-dimethylhydroxylamine and the resulting N-methoxy-N-methylcarboxamide derivative reacted with a compound of formula (V), suitably an organolithium or Grignard reagent, to provide a compound of formula (II). Where $R_3$ is ethnyl, it is preferably protected in the compound of formula (V) which is suitably lithium (trimethylsilyl) acetylene. The trimethylsilyl protecting group is preferably removed after reaction of the compounds of formulae (II) and (III) by treatment with aqueous sodium hydroxide.

Where $R_3$ is cyclopropyl, a compound of formula (VI) in which L is preferably chloro or bromo may be treated with cyclopropyltrimethylsilane in the presence of aluminium trichloride in dichloromethane.

Where $R_3$ is $CH_2CN$, a compound of formula (VI) in which L is preferably $C_{1-4}$ alkoxy may be treated with a suitable organolithium or Grignard reagent, for example the reaction product of acetonitrile and lithium diisopropylamide. It will be appreciated that the resulting compound of formula (II) will be in the form of the lithium enolate salt.

A compound of formula (VI) may alternatively be reacted with a compound of formula (III) wherein $R_2'$ is $OR_4$, in acetonitrile as solvent, in the presence of a base such as pyridine or triethylamine, and the resulting derivative of formula (IVa) treated with a chlorinating or brominating agent to provide a compound of formula (IV) in which $R_2$ is $OR_4$.

Novel compounds of formulae (II) and (Iva) also form part of the invention.

Compounds of formula (VI) where $R_1$ represents group (A) may conveniently be prepared by cyclising a compound of formula (VII):

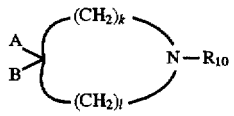

(VII)

in which (i) A represents a group convertible to COCl and B represents —$(CH_2)_jL_1$ where $L_1$ is a leaving group or A and $L_1$ together represent —COO—; one of j, k and l is 1 and the other two independently represent an integer of 2 to 4, and $R_{10}$ represents hydrogen or an N-protecting group; to give a compound of formula (VIIa):

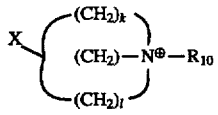

(VIIa)

in which X represents a group convertible to COCl or COBr, $Z^-$ is an anion and the remaining variables are as previously defined;

or (ii) A represents an electron withdrawing group, B represents hydrogen and $R_{10}$ represents $—(CH_2)_j L_2$ where $L_2$ is a leaving group; one of k and l is 1 and the other and j independently represent an integer of 2 to 4; to give a compound of formula (VIIb):

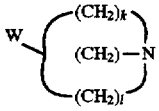

(VIIb)

in which W represents an electron withdrawing group or X and the remaining variables are as previously defined;

and thereafter, optionally or as necessary, removing any $R_{10}$ N-protecting group, converting W to X and converting X to COCl or COBr.

The deprotection, conversion and interconversion steps may be carried out in any appropriate order.

Examples of the leaving groups $L_1$ and $L_2$ include halo such as bromo or chloro, tosyloxy and mesyloxy.

Examples of $R_{10}$ when an N-protecting group include benzyl and substituted benzyl.

Examples of A and X when groups convertible to COCl or COBr include a $C_{1-4}$ alkoxycarbonyl, benzyloxycarbonyl and cyano.

The cyclisation reaction is a nucleophilic substitution which may be carried out under conventional conditions appropriate to the groups A and B. Thus, when B is $(CH_2)_jBr$ and A is $C_{1-4}$ alkoxycarbonyl, the cyclisation is carried out in an inert solvent such as toluene or ether at elevated temperature. When B is $(CH_2)_jOTos$ or $(CH_2)_jOMes$, it is preferably obtained by treatment of a $(CH_2)_jOH$ group with a suitable reagent such as tosyl chloride or mesyl chloride, in a base such as pyridine, whereupon the cyclisation may proceed at ambient temperature, or at elevated temperature in an inert solvent such as toluene. When A and $L_1$ together represent —COO—, the cyclisation may be carried out in a lower alkanol such as ethanol in the presence of acid such as hydrogen bromide. In the resulting compound of formula (VIIa), X will be an alkoxycarbonyl group corresponding to the lower alkanol used for the cyclisation.

Where $R_{10}$ is an N-protecting group such as benzyl, this may be removed by conventional hydrogenation, preferably catalytically over a suitable catalyst such as Pd/C.

Examples of A when an electron withdrawing group include $C_{1-4}$ alkoxycarbonyl and cyano.

When A is an electron withdrawing group such as $C_{1-4}$ alkoxycarbonyl, B is hydrogen and $R_{10}$ is $—(CH_2)_jL_2$ where $L_2$ is, for example, chloro, the cyclisation may be effected by treatment of the compound of formula (VII) with lithium diisopropylamide.

Compounds of formula (VI) where $R_1$ represents group (B) may conveniently be prepared by:

(a) cyclising a compound of formula (VIIIa):

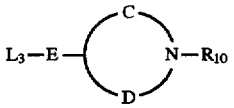

(VIIIa)

where $R_{10}$ is hydrogen or an N-protecting group, and either C is one, D is another and E is the remainder of $—(CH_2)_r—$, $—(CH_2)_s—$ and $—(CH_2)_t—CHX—CH_2—$ or groups convertible thereto, X is a group convertible to COCl or COBr and $L_3$ is a leaving group, or C is one and E is the other of $—(CH_2)_r—$ and $—(CH_2)_s—$ or groups convertible thereto and D represents $—(CH_2)_t—CHX—CH_2—$ where X and $L_3$ together represent —COO—, and thereafter, optionally or as necessary and in any appropriate order, converting C, D and E to $—(CH_2)_r—$, $—(CH_2)_s—$ and $—(CH_2)_t—CHX—CH_2—$, removing any $R_{10}$ protecting group, and converting X to COCl or COBr; or (b) cyclising a compound of formula (VIIIb):

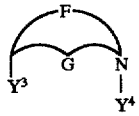

(VIIIb)

where F is one and G is the other of $—(CH_2)_r—$ and $—(CH_2)_s—$ or groups convertible thereto, and one of $Y^3$ and $Y^4$ is $—(CH_2)_m—K$ and the other is $—(CH_2)_nW$ or $(CH_2)_n L_4$ where K and W are electron withdrawing groups, $L_4$ is a leaving group, m is 1 or 2 and n is 0 or 1 with the provisos that, when $Y^4$ is $—(CH_2)_nW$, n is 1, and $Y^4$, is not $—(CH_2)_n L_4$, and thereafter, optionally or as necessary and in any appropriate order, hydrolysing and decarboxylating the cyclisation product and converting the carbonyl group to —CHX where X is a group convertible to COCl or COBr, converting W to X as defined, converting X to COCl or COBr, converting F and G to $—(CH_2)_r—$ and $—(CH_2)_s—$ as appropriate, m and n being such that the desired compound of formula (VI) is obtained.

Examples of leaving groups $L_3$ include halo such as chloro and hydroxy. Examples of $L_4$ include those given for $L_3$ or $C_{1-4}$ alkoxy such as ethoxy. Examples of electron withdrawing groups K and W include $C_{1-4}$ alkoxycarbonyl and cyano. In the group $—(CH_2)_t—CHX—CH_2—$, examples of X include hydroxy and cyano.

In the process variant (a), where $L_3$ is hydroxy and D is $—CHOH—CH_2—$, the cyclisation may be carried out by pyrolysis, by the method of D. O. Spry and H. S. Aaron, J. Org. Chem., 1969, 34, 3674, to yield a compound where X is hydroxy.

Where E is $—(CH_2)_rCOCH_2—$, the cyclisation may be carried out under basic conditions where $R_{10}$ is benzyl (F. I. Carrol, A. M. Ferguson, and J. B. Lewis, J. Org. Chem. 31, 2957, 1966). The resulting ketone may be reacted with tosylmethyl isocyanide to yield a compound where X is cyano.

Where $L_3$ and X together represent —COO—, the cyclisation is a rearrangement reaction which can be carried out under acid conditions in a polar solvent, such as hydrogen bromide in ethanol, at ambient temperature, to yield a compound where X is a carboxy ester group. It is preferred to protect the nitrogen atom with an $R_{10}$ N-protecting group such as benzyl, which may be subsequently removed by hydrogenation over a suitable catalyst such as Pd/C. In the compound of formula (VIIIa) where t=O, C is $—CH_2—$ and E is $—(CH_2)_2—$, the cyclisation product is the endo isomer.

In the process variant (b), where $Y^3$ and $Y^4$ both contain carboxy ester groups the cyclisation is a Dieckmann reaction which is catalysed by a base such as potassium t-butoxide at elevated temperature in a solvent such as toluene.

The resulting β-keto ester is hydrolysed and decarboxylated under conventional conditions such as heating at reflux in dilute hydrochloric acid.

The carbonyl group may then be reduced to an X hydroxy group with a suitable reducing agent such as sodium borohydride in ethanol at ambient temperature, or sodium in ethanol at elevated temperature, such as the boiling point of the solvent, under an inert atmosphere sphere such as nitrogen, depending upon the stereo-chemistry required.

Alternatively, the carbonyl group may be converted directly to an X cyano group with a suitable reagent such as tosylmethylisocyanide in an inert solvent such as dry dimethoxyethane, at depressed temperature, under basic conditions such as the presence of potassium t-butoxide.

In process variant (b) where $Y^3$ and $Y^4$ both contain cyano groups the cyclisation is a Thorpe reaction which is catalysed by a base such as potassium t-butoxide at elevated temperature in a solvent such as toluene.

The resulting β-keto nitrile is hydrolysed and decarboxylated under conventional conditions such as heating at reflux in dilute hydrochloric acid.

Where $Y^3$ is $—(CH_2)_nL_4$, the cyclisation may be carried out as described in EP-A No. 0094742 under basic conditions such as sodium hydride and potassium t-butoxide, in an inert polar solvent such as dimethyl formamide.

The conversion of K, W and X to COCl or COBr may be carried out conventionally.

An X hydroxy group may be converted to cyano by first converting it to a good laving group such as mesyloxy or tosyloxy and then displacing it with cyanide ion.

An X carboxy group may be obtained by conventional de-esterification of an X, K or W alkoxycarbonyl group. Where $R_{10}$ is an N-protecting group and X, K or W is a benzyloxycarbonyl group, the de-esterification and deprotection steps may conveniently be effected simultaneously by conventional hydrogenation such as described above. Alternatively, an X carboxy group may be obtained by conventional acid hydrolysis of an X, K or W cyano group. A carboxy group may be treated with thionyl chloride at elevated temperature to give the chlorocarbonyl group, COCl or with thionyl bromide to give the bromocarbonyl group, COBr.

Compounds of formula (VII) may be prepared conventionally.

Where A is $C_{1-4}$ alkoxycarbonyl, B is $(CH_2)_jL_1$ and $R_{10}$ is hydrogen or an N-protecting group, the compound of formula (VII) may be prepared by treating a compound of formula (IX):

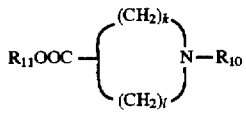

(IX)

where $R_{11}$ is $C_{1-4}$ alkyl and the remaining variables are as previously defined, with lithium diisopropylamide, prepared in situ from diisopropylamine and n-butyllithium followed by reaction with a compound $L_5(CH_2)_jL_1$ where $L_5$ is a leaving group, in an inert solvent such as ether at depressed to elevated temperature. Both $L_1$ and $L_5$ are suitably bromo.

Where A and $L_1$ together represent —COO— and j is 2, the compound of formula (VII) may be prepared by reacting the compound of formula (IX), treated with lithium diisopropylamide as before, with ethylene oxide in an inert solvent such as ether at depressed to elevated temperature.

Alternatively, the compound of formula (VII) where A and $L_1$ together represent —COO, j is 2, k is 2 and l is 1 may be prepared by a 1,3-dipolar cycloaddition reaction which involves reacting a compound of formula (X):

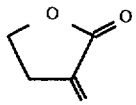

(X)

with a compound of formula (XI):

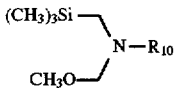

(XI)

in which $R_{10}$ is an N-protecting group in the presence of a catalytic amount of trifluoroacetic acid.

Where A is an electron withdrawing group such as $C_{1-4}$ alkoxycarbonyl, B is hydrogen and $R_{10}$ is $(CH_2)_jL_2$, the compound of formula (VII) may be prepared by reacting the compound of formula (IX) where $R_{10}$ is hydrogen with a compound $L_5(CH_2)_jL_2$ where $L_5$ is as previously defined, in a solvent such as acetone in the presence of a base such as potassium carbonate. The leaving group $L_5$ is preferably bromo and $L_2$ is preferably chloro.

Compounds of formula (IX) are known compounds or may be prepared by analogous methods to those for preparing known compounds. The compound of formula (IX) where k is 2, l is 1 and $R_{10}$ is benzyl may be prepared by the cyclisation of di-$C_{1-4}$ alkyl itaconate in the appropriate alkanol with benzylamine at elevated temperature, followed by reduction of the resulting oxo group at the 2-position of the pyrrolidine ring with $BH_3$ in tetrahydrofuran, at ambient to elevated temperature.

Intermediates of formulae (VIIIa) and (VIIIb) are known compounds (e.g. as described in EP-A-0094742) or may be prepared analogously.

Intermediates of formula (VIIa) where X and $L_3$ together represent —COO—, t=O, C is is $—(CH_2)_2—$ and E is $—CH_2—$ are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

The compound of formula (VIIIa) where X and $L_3$ together represent —COO—, t=O, C is $—CH_2—$ and E is $—(CH_2)_2—$ may be prepared by a 1,3-dipolar cycloaddition reaction of a compound of formula (XI) with 5,6-dihydro-2H-pyran-2-one in the presence of a catalytic amount of trifluoroacetic acid.

Intermediates of formula (VIIIa) where $L_3$ is a leaving group are described in, for example, Spry et al., J. Org. Chem., 1969, 34, 3674 and Hasse et at., Chem. Ber., 1960, 93, 1686.

Intermediates of formula (VIIIb) are described in, for example, Martell et al., J. Pharm. Sci., 1963, 52(4), 331 Sternbach et al., J.A.C.S., 1952, 74, 2215, Thill et al., J. Org. Chem., 1968, 33, 4376 and EP-A No. 0094742.

Compounds of formula (III) are known compounds or may be prepared by analogous methods to those for preparing known compounds. Certain compounds of formula (III) are commercially available.

Compounds of formulae (X) and (XI) may be prepared conventionally. Thus, a compound of formula (X) may be obtained by the reaction of γ-butyrolactone with ethyl formate in the presence of base such as sodium hydride followed by reaction of the resulting formyl derivative (as the enol salt) with formaldehyde. A compound of formula (XI) may be obtained by the reaction of the primary amine $R_{10}NH_2$ successively with chloromethyltrimethylsilane and formaldehyde followed by methanol and anhydrous potassium carbonate.

Where applicable, an exo isomer may be obtained by epimerisation of a corresponding endo isomer and vice versa, the epimerisation reaction being effected by standard procedures at any convenient stage in the process.

The different stereoisomeric forms of compounds of formula (I) may be separated one from the other by the usual methods, for example using chromatographic methods. Enantiomers may be separated using chiral resolving agents such as (S)-(+)- and (R)-(−)-1,1'-binaphthyl-2,2'-diyl hydrogen phosphate, or chiral chromatography, or any given isomer may be obtained by stereospecific or asymmetric synthesis.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, or hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg, for example 0.2 to 50 mg and such unit doses may be administered more than once a day, for example two or three times a day, so that the total daily dosage is in the range of about 0.01 to 5 mg/kg and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

(±) 3-Cyano-1-azabicyclo[2.2.2]octane (D1)

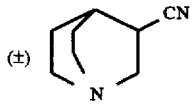

(D1)

A mixture of 3-quinuclidinone (12.5 g; 0.10 moles), tosylmethyl isocyanide (25.4 g; 0.13 moles) and dry ethanol (10 ml; 0.17 moles) in dry dimethoxyethane (350 ml) was cooled in ice and treated portionwise with potassium t-butoxide (28.0 g; 0.25 moles) while maintaining the temperature between 5° C. and 10° C. After addition was complete the ice bath was removed and stirring was continued for a further 30 min. The reaction was then heated at 40° C. for 2.5 h. After cooling the precipitate was filtered off and the flitrate concentrated in vacuo. Purification on neutral alumina (Brockmann grade 1) using 2% methanol in ethyl acetate as eluant afforded the title compound (D1) as a syrup (10.0 g; 74%) which crystallised on cooling.

DESCRIPTION 2

(±) 1-Azabicyclo[2.2.2]oct-3-yl-N-methoxycarboxamide (D2)

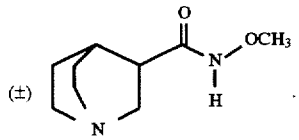

(D2)

A solution of (±) 3-cyano-1-azabicyclo[2.2.2]octane (D1) (15 g, 0.1103 mole) in concentrated hydrochloric acid (300 ml) was heated under reflux for 4 h and then concentrated in vacuo to leave a yellow gum. This was dissolved in methanolic hydrogen chloride (200 ml) and heated under reflux for 2 h, then concentrated in vacuo to give an orange oil. This oil was treated with excess saturated potassium carbonate solution and extracted with chloroform (3×100 ml). The combined extracts were dried ($Na_2SO_4$) and evaporated to give the methyl ester (18 g) as a yellow oil. A solution of this ester (17.5 g, 0.956 mole) in 8M hydrochloric acid (200 ml) was heater under reflux for 3 h. The reaction was then concentrated in vacuo to a solid which was dissolved in thionyl chloride (250 ml) and heated under reflux for 1 h when the copious evolution of sulphur dioxide and hydrogen chloride ceased. The reaction was then concentrated in vacuo to a gum, which was freed from excess thionyl chloride by co-evaporation with toluene. The residue was dissolved in dry acetonitrile (700 ml) under an atmosphere of nitrogen and treated with methoxylamine hydrochloride (8.14 g, 0.0975 mole). After cooling to 0° C. triethylamine (40.8 ml, 0.293 mole) was added dropwise over 0.5 h and the mixture was stirred at 0° C. for 3 h. Triethylamine hydrochloride was removed by filtration, the solvent was removed in vacuo and the residue partitioned between saturated aqueous potassium carbonate solution (200 ml) and chloroform (5×150 ml). The combined organic extracts were dried ($Na_2SO_4$) and evaporated to a gum, which was chromatographed on neutral alumina using 1–10% methanol/chloroform as eluant to afford the title compound (D2) (8.28 g, 54%) as a semi-crystalline solid.

$^1$H NMR ($CDCl_3$) δ: 1.41 (1H, m), 1.63 (2H, m), 1.95 (2H, m), 2.70–3.12 (6H, m), 3.35 (1H, m), 3.76 (3H, s), 6.6 (1H, br).

DESCRIPTION 3

(±) Ethyl 1-(2-chloroethyl)-3-piperidylcarboxylate (D3)

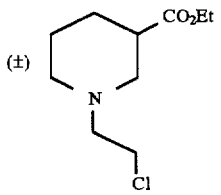

(D3)

A solution of ethyl 3-piperidylcarboxylate (100 g, 0.64 mole) in acetone (800 ml) was treated with 1-bromo-2-chloroethane (106.5 ml, 1.28 mole) and anhydrous potassium cabonate (138 g, 1.00 mole) and the mixture stirred at room temperature for 24 h. The mixture was concentrated in vacuo and the residue treated with water (300 ml) and extracted with ether (2×200 ml). The combined ether extracts were dried ($Na_2SO_4$) and concentrated in vacuo to leave a yellow oil, which was purified by chromatograpny on silica gel eluting with 50% ether/60–80 petrol to give the title compound (D3) as a pale yellow oil (78.2 g, 56%).

$^1$H Nmr ($CDCl_3$) δ1.25 (3H, t, J=7Hz), 1.40–3.10 (11H, m), 3.58 (2H, t, J=7 Hz), 4.15 (2H, q, J=7Hz)

DESCRIPTION 4

(±) Ethyl 1-azabicyclo[3.2.1]oct-5-ylcarboxylate (D4)

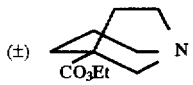

(D4)

A solution of diisopropylamine (33.6 ml, 0.24 mole) in dry ether (1500 ml) at −65° C. under nitrogen was treated with 1.5M n-butyllithium in hexane (150 ml, 0.225 mole) and the solution stirred for 15 mins, before adding N,N,N',N'-tetramethylethylenediamine (68 ml, 0.45 mole). After stirring for a further 15 mins, the solution was treated with a solution of ethyl 1-(2-chloroethyl)-3-piperidylcarboxylate (D3, 44.7 g, 0.204 mole) in dry ether (100 ml) and the mixture allowed to warm up to room temperature over 2 h. The reaction mixture was treated with potassium carbonate solution (300 ml) and the ether layer separated, dried ($Na_2SO_4$) and concentrated in vacuo to leave an orange oil. This was purified by chromatography on silica gel eluting with 10% methanol/chloroform to give the title compound (D4) as a yellow oil (31.9, 84%), b.p. 120°–130° $C._{0.4mmHg}$ (Kugelröhr apparatus).

$^1$H Nmr ($CDCl_3$) δ1.25 (3H, t, J=7Hz), 1.10–2.20 (6H, m), 2.60–3.25 (6H, m), 4.20 (2H, q, J=7Hz)

DESCRIPTION 5

(±) 1-Azabicyclo[3.2.1]oct-5-yl-N-methoxy-N-methylcarboxamide (D5)

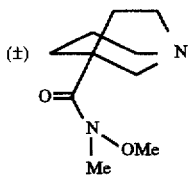

(D5)

(±) Ethyl-1-azabicyclo[3.2.1]oct-5-ylcarboxylate (D4, 5 g, 0.027 mole) in hydrochloric acid (5N, 150 ml) was heated under reflux for 1.5 h. The reaction was then concentrated in vacuo to a hygroscopic solid which was dissolved in thionyl chloride (100 ml) and heated under reflux for 0.5 h. The mixture was then concentrated in vacuo to a gum, which was freed from excess thionyl chloride by co-evaporation with toluene. The residue was dissolved in absolute chloroform (100 ml) and treated with N,O-dimethylhydroxylamine hydrochloride (2.92 g, 0.030 mole). After cooling to 0° C. pyridine (10.9 ml, 0.135 mole) was added dropwise. The reaction was allowed to warm to room temperature and stirred for 1 h. The reaction mixture was poured into saturated aqueous potassium carbonate solution (100 ml) and the mixture was extracted with chloroform (4×100 ml).

The combined organic extracts were dried ($Na_2SO_4$) and evaporated to give an oil which was distilled in vacuo to afford the title compound (D5) (3.77 g, 69%) b.p. 160° C. at 0.5 mmHg.

$^1$H Nmr ($CDCl_3$) δ: 1.47 (1H, m), 1.68–2.13 (7H, m), 2.78–3.15 (6H, m), 3.17 (3H, s), 3.67 (3H, s).

DESCRIPTION 6

(±) 1-Azabicyclo[3.2.1]oct-5-yl trimethylsilylethynyl ketone (D6)

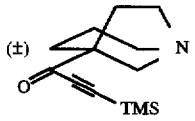

(D6)

n-Butyllithium (7.3 ml of a 1.6M solution in hexane, 0.0117 mole) was added dropwise to (trimethylsilyl) acetylene (1.57 ml, 0.0111 mole) in dry THF (50 ml) at −70° C. The resulting solution was stirred at −70° C. for 0.5 h then added dropwise by cannula to (±) 1-azabicyclo[3.2.1]oct-5-yl-N-methoxy-N-methylcarboxamide (D5, 1.83 g, 0.0092 mole) in dry THF (50 ml) at −70° C. The mixture was allowed to warm to −50° C., stirred at this temperature for 1 h, then poured into ice-cold 1M hydrochloric acid. After 15 mins at 0° C. the mixture was made just basic by addition of potassium carbonate and extracted with chloroform (3×100 ml). The combined extracts were dried ($Na_2SO_4$) and evaporated to give the title compound (D6) as a clear mobile oil (1.65 g, 76%).

$^H$ Nmr ($CDCl_3$) δ: 0.24 (9H, s), 1.00–1.91 (5H, m), 2.29 (1H, m), 2.70–3.28 (6H, m).

DESCRIPTION 7

(±) 1-Azabicyclo[3.2.1]oct-5-yl -trimethylsilylethynyl ketone-O-methyloxime (D7)

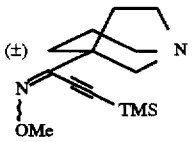

(D7)

1-Azabicyclo[3.2.1]oct-5-yl trimethylsilylethynyl ketone (D6, 0.85 g, 0.0036 mole) was added to a mixture of methanol (50 ml) and glacial acetic acid (1.5 ml). Methoxylamine hydrochloride (0.36 g, 0.0043 mole) was added and the reaction mixture stirred at room temperature for 18 h then evaporated under reduced pressure. Saturated potassium carbonate (25 ml) was added to the residue and the mixture was extracted with chloroform (4×50 ml). The combined organic extracts were dried ($Na_2SO_4$) and evaporated to give the title compound (D7) as a 6:1 mixture of cis and trans oxime ethers (0.77 g, 81%).

$^1$H Nmr (major isomer, $CDCl_3$): 0.25 (9H, s), 1.53 (1H, m), 1.68–1.95 (4H, m), 2.07 (1H, m), 2.72–3.16 (6H, m), 3.96 (3H, s).

$^{13}$C Nmr (major isomer, $CDCl_3$): −0.29, 19.77, 34.49, 35.02, 47.61, 52.08, 54.57, 62.45, 63.47, 93.86, 107.40, 145.41

DESCRIPTION 8

(±) 1-Azabicyclo[3.2.1]oct-5-yl-N-methoxycarboxamide (D8)

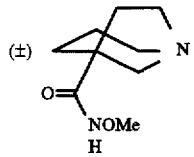

(D8)

(±) Ethyl-1-azabicyclo[3.2.1]oct-5-ylcarboxylate (D4, 7.33 g, 0.040 mole) in hydrochloric acid (8N, 100 ml) was heated under reflux for 4 h and then concentrated in vacuo to give a white solid which was dissolved in thionyl chloride (100 ml) and heated under reflux for 1.5 h. The mixture was concentrated in vacuo to a gum, which was freed from excess thionyl chloride by co-evaporation with toluene. The residue was dissolved in dry acetonitrile (200 ml) and methoxylamine hydrochloride (3.51 g, 0.042 mole) was added. After cooling to −20° C., triethylamine (27.9 ml, 0.200 mole) was added dropwise over 0.5 h and the reaction mixture was allowed to warm to room temperature overnight. The solvent and excess triethylamine were removed in vacuo and the residue was partitioned between saturated aqueous potassium carbonate solution (100 ml) and chloroform (5×100 ml). The combined organic extracts were dried ($Na_2SO_4$) and evaporated to a gum, which was chromatographed on neutral alumina using 3–15% methanol/chloroform as eluant to afford the title compound (D8) (2.86 g, 39%) as a low-melting solid.

$^1$H Nmr ($CDCl_3$) δ: 1.55 (1H, m), 1.67–2.00 (4H, m), 2.12 (1H, m), 2.73–3.01 (5H, m), 3.12 (1H, m), 3.76 (3H, s), 5.60 (1H, broad).

DESCRIPTION 9

(±) exo-Ethyl 1-azabicyclo[2.2.1]hept-3-ylcarboxylate (D9)

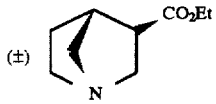

(D9)

(±) exo-Ethyl 1-benzyl-1-azoniabicyclo[2.2.1]hept-3-ylcarboxylate bromide (EP A No. 0257741 Description 9) (54 g 0.16 mole) was dissolved in ethanol (400 ml) and hydrogenated over 10% Pd-C (8.5 g) at atmospheric pressure and 25° C. After 2 h the solution was filtered and concentrated in vacuo to leave a gum. This was partitioned between chloroform and saturated aqueous potassium carbonate solution and the organic phase separated, dried ($Na_2SO_4$) and concentrated in vacuo to leave a gum. This gum was distilled to give the title compound (D9) as a colourless oil (23 g, 85%) b.p. 150° C. at 0.5 mmHg.

$^1$H Nmr ($CDCl_3$) δ: 1.10–1.20 (1H, m), 1.25 (3H, t, J=7Hz), 1.54–1.67 ($^1$H, m), 2.15–2.25 (1H, m), 2.28–2.35 (1H, m), 2.38–2.50 (1H, m), 2.60–2.67 (1H, m), 2.70–2.90 (3H, m), 2.93–3.03 (1H, m), 4.13 (2H, q, J=7Hz).

DESCRIPTION 10

(±) exo-1-Azabicyclo[2.2.1]hept-3-yl-N-methoxycarboxamide (D10)

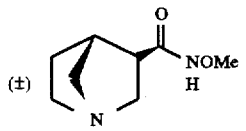

(D10)

(±) exo-Ethyl-1-azabicyclo[2.2.1]hept-3-ylcarboxylate (D9, 1 g, 0.0059 mole) was converted to the acid chloride hydrochloride salt and treated with methoxylamine hydrochloride (0.54 g, 0.0065 mole) and triethylamine as in the method of Description 8 to give the title compound (D10) (0.40 g, 40%) as a low melting solid.

$^1$H Nmr ($CDCl_3$) δ: 1.18 (1H, m), 1.63 (1H, m), 2.40–2.58 (2H, m), 2.63–2.98 (5H, m), 3.06 (1H, m), 3.73 (3H, s).

DESCRIPTION 11

N-Benzyl-N-[(trimethylsilyl)methyl]amine (D11)

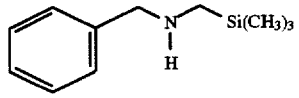

(D11)

A mixture of chloromethyltrimethylsilane (325 g, 370 ml, 2.65 mole) and benzylamine (835 g, 850 ml, 7.78 mole) was heated at 120°C. (oil bath temperature) for 2 h. A white solid began appearing after only 10 minutes and a viscous mixture eventually resulted. The reaction mixture was allowed to cool, then basified with potassium carbonate solution and extracted twice with ether. The combined extracts were dried ($Na_2SO_4$) and concentrated in vacuo to leave a yellow oil, which was purified by distillation. The excess benzylamine was removed in the first fractions (b.p. 47°–62°C. at 2 mmHg). The title compound (D11) was obtained as a colourless oil (380 g, 74%) b.p. 75°–80°C. at 2 mmHg.

$^1$H Nmr ($CDCl_3$) δ: 0.10 (9H, s), 1.40 (1H, br.s, NH), 2.10 (2H, s), 3.85 (2H, s), 7.27–7.43 (5H, m)

DESCRIPTION 12

N-Benzyl-N-(methoxymethyl)-N-[(trimethylsilyl) methyl]amine (D12)

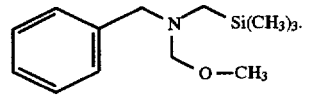

(D12)

A stirred 37% aqueous formaldehyde solution (230 g, 215 ml, 2.8 mole) was cooled to −5° C. and treated dropwise over 20 minutes with N-benzyl-N-[(trimethylsilyl)methyl] amine (D11, 380 g, 1.96 mole), whilst keeping the temperature between −5° and 0° C. After completing the addition, the mixture was treated with methanol (230 ml), saturated with potassium carbonate and stirred at room temperature for 2 h. The mixture was treated with ether (500 ml) and the organic phase separated, dried ($K_2CO_3$) and concentrated in vacuo to give a colourless oil (480 g), which was about 75% title compound (D12). This material was used in the next stage without purification.

$^1$H Nmr ($CDCl_3$) δ: 0.10 (9H, s), 2.23 (2H, s), 3.30 (3H, s), 3.82 (2H, s), 4.05 (2H, s), 7.25–7.40 (5H, m)

DESCRIPTION 13

α-Formyl-γ-butyrolactone sodium salt (D13)

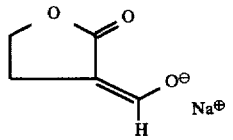

(D13)

A stirred suspension of sodium hydride (300 g of 80% oil dispersion, 10 moles) in dry ether (8l) under nitrogen was treated slowly with absolute ethanol (60 ml, 1.1 mole), followed immediately by a mixture of ethyl formate (808 ml, 10 moles) and γ-butyrolactone (770 ml, 10 moles) over about 1.25 h. The rate of addition of the reagents was regulated to give a steady reflux and evolution of hydrogen (about 220 l). After completing the addition, the mixture was stirred for a further 0.5 h and the solid then filtered off, washed with ether and dried in vacuo to give the title compound (D13) as a white solid (1.32 kg, 97%).

DESCRIPTION 14

α-Methylene-γ-butyrolactone (D14)

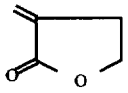

(D14)

A stirred suspension of paraformaldehyde (270 g, 9.0 mole) in THF (3.5 L) at room temperature in a 20 L flask under nitrogen was treated with α-formyl-γ-butyrolactone sodium salt (D13, 270 g, 2.0 mole). The mixture was then immediately heated to reflux temperature for 1 h. Evolution of a small quantity of gas was observed. The mixture was cooled to around 10° C., treated with saturated aqueous potassium carbonate solution (500 ml) and ether (1.5 L), and the organic layer separated, dried ($Na_2SO_4$) and concentrated in vacuo to leave a pale yellow oil. This material was distilled to give the title compound (D14) as a colourless oil (125 g, (64%) b.p. 76°–80° C. at 8 mmHg.

$^1$H Nmr ($CDCl_3$) δ: 2.95–3.03 (2H, m), 4.40 (2H, t, J=7Hz), 5.69 (1H, t, J=3Hz), 6.25 (1H, t, J=3Hz)

DESCRIPTION 15

(±)-7-Benzyl-7-aza-2-oxaspiro[4.4]nonan-1-one (D15)

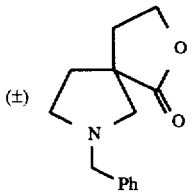

(D15)

A stirred solution of N-benzyl-N-(methoxymethyl)-N-[(trimethylsilyl)methyl]amine (D12, 160 g of 75% purity, assume 0.51 mole) and α-methylene-γ- butyrolactone (D14, 50 g, 0.51 mole) in dichloromethane (11 L) under nitrogen was cooled to 0° C. and then treated with a 1M solution of trifluoroacetic acid in dichloromethane (50 ml, 0.05 mole), keeping the temperature below 5° C. The reaction mixture was allowed to warm to room temperature over 2 h, then washed with saturated sodium bicarbonate solution. The aqueous wash was extracted with dichloromethane and the organic solutions then combined, washed with brine, dried ($Na_2SO_4$) and concentrated in vacuo to leave a pale yellow oil. This was distilled in vacuo to give the title compound (D15) as a colourless oil (96 g, 81%) b.p. 160°–170° C. at 1 mmHg.

$^1$H Nmr ($CDCl_3$) δ: 1.77–1.92 (1H, m), 2.15–2.40 (3H, m), 2.48–2.78 (3H, m), 2.85–2.98 (1H, m), 3.55–3.70 (2H, m), 4.10–4.30 (2H, m), 7.15–7.35 (5H, m)

DESCRIPTION 16

Ethyl 1-benzyl-1-azoniabicyclo[2.2.1]hept-4-ylcarboxylate bromide (D16)

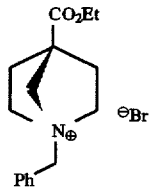

(D16)

A stirred solution of 7-benzyl-7-aza-2-oxaspiro[4.4]nonan-1-one (D15, 96 g, 0.42 mole) in ethanol (150 ml) was saturated with hydrogen bromide gas and then left to stand for 18 h. The solution was concentrated in vacuo and the residue basified with saturated potassium carbonate solution and extracted with chloroform. The organic extract was dried ($Na_2SO_4$) and concentrated in vaeuo to leave a pale brown oil. This was treated with ether and the resulting solid filtered off, washed with ether and dried to give the title compound (D16) as a white solid (130 g, 91%).

DESCRIPTION 17

Ethyl 1-azabicyclo[2.2.1]hept-4-ylcarboxylate hydrobromide salt (D17)

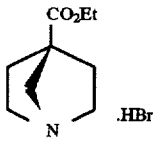

(D17)

A suspension of ethyl 1-benzyl-1-azoniabicyclo[2.2.1]hept-4-ylcarboxylate bromide (D16, 130 g, 0.38 mole) in ethanol (500 ml) was hydrogenated over 10% palladium on charcoal catalyst (8 g) at atmospheric temperature and pressure for 18 h. The catalyst was removed by filtering through celite, washing several times with hot ethanol, and the filtrate concentrated in vacuo to give the title compound (D17) as a crystalline white solid (80.1 g, 84%).

$^1$H Nmr ($CD_3OD$) δ: 1.3 (3H, t, J=7Hz), 2.0–2.18 (2H, m), 2.3–2.5 (2H, m), 3.35–3.5 (2H, m), 3.45 (2H, s), 3.5–3.7 (2H, m), 4.25 (2H, q, J=7Hz)

DESCRIPTION 18

1-Azabicyclo [2.2.1 ]hept-4-yl-N-methoxycarboxamide (D18)

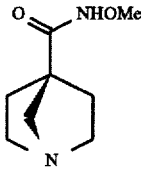

(D18)

Ethyl 1-azabicyclo[2.2.1]hept-4-ylcarboxylate hydrobromide salt (D17, 16.85 g, 0.067 mole) was converted to the acid chloride hydrochloride salt and treated with methoxylamine hydrochloride (6.19 g, 0.074 mole) and triethylamine as in the method of Description 8 to give the title compound (D18) as a pale brown crystalline solid (4.60 g, 40%) m.p. 129°–134° C.

$^1$H Nmr ($CDCl_3$) δ: 1.48 (2H, m), 1.97 (2H, m), 2.66 (4H, m), 3.05 (2H, m), 3.80 (3H, s).

DESCRIPTION 19

(±) 1-Azabicyclo[2.2.2oct-3-yl cyclopropyl ketone (D19)

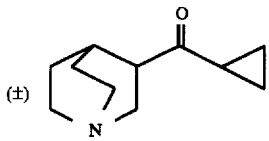

(D19)

(±) 3-Cyano-1-azabicyclo[2.2.2]octane (D1) (5 g, 0.0368 mole) was converted to the acid chloride hydrochloride salt as in the method of Description 2. To a mixture of this material (1 g, 0.0048 mole) and cyclopropyltrimethylsilane* (0.54 g, 0.0047 mole) in dichloromethane (100 ml) at room temperature was added aluminium chloride (1.27 g, 0.0095 mole) in portions with cooling. After stirring at room temperature for 16 h the reaction mixture was poured into saturated potassium carbonate (75 ml) and extracted with chloroform (3×75 ml). The combined extracts were dried ($Na_2SO_4$) and evaporated to an oil which was chromatographed on silica gel using 10% methanol/chloroform as eluant to give the ketone (D19) as a pale yellow oil (0.16 g, 19%).

* M.Grignon-Dubois, J. Dunogues and R. Calas, Synthesis, 1976, 737.

$^1$H Nmr ($CDCl_3$) δ: 0.76–1.06 (4H, m), 1.33 (2H, m), 1.62 (2H, m), 1.89 (1H, m), 2.60–2.92 (6H, m), 3.22–3.49 (2H, m).

$^{13}$C Nmr ($CDCl_3$) δ: 10.60, 10.92, 19.83, 22.14, 24.17, 27.12, 46.93, 47.17, 47.93, 49.89, 211.37

DESCRIPTION 20

(±) cis-2-Benzyl-hexahydropyrano[3,4-c]pyrrole-4 (1H)-one (D20)

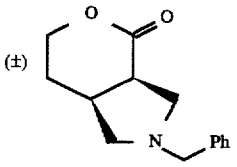

(D20)

To a stirred solution of 5,6-dihydro-2H-pyran-2-one* (136 g, 1.39 mole) in dichloromethane (2 L) at −20° C. was added N-benzyl-N-(methoxymethyl)-N-trimethylsilylmethyl amine (80% pure) (D12, 450 g, 1.5 mole). To this solution was added trifluoroacetic acid in dichloromethane (140 ml, 1 molar solution) at −20° C. The reaction was then transferred at −20° C. under a small positive pressure of nitrogen via a double ended needle to a second flask on a water bath at 30° C. As the cold mixture warmed up an exothermic reaction occurred and the rate of addition was controlled to maintain gentle reflux. When addition was complete and the reaction had subsided the solution was allowed to stand at room temperature for 2 h. The reaction was then washed with saturated aqueous potassium carbonate solution, dried ($Na_2SO_4$) and concentrated in vacuo to a gum. Vacuum distillation afforded the title compound as a single main fraction b.p. 180°–190° C. $_{0.5mmHg}$ (D20, 180.9 g, 0.73 mole, 56%).

*Org. Syn., Vol. 56, P49.

$^1$H NMR ($CDCl_3$) δ: 1.55–1.72 (1H, m), 1.95–2.10 (1H, m), 2.23–2.34 (1H, m), 2.63–3.0 (4H, m), 3.05–3.2 (1H, m), 3.55 and 3.65 each (1H, d, J=12Hz), 4.22 (1H, t, J=12Hz), 4.35–4.48 (1H, m), 7.30 (5H, brs).

$^{13}$C NMR $CDCl_3$ δ: 28.4, 35.1, 42.1, 57.5, 59.6, 60.2, 67.2, 127.2, 128.4, 128.7, 138.6, 173.3

DESCRIPTION 21

(±) endo

Ethyl-1-azabicyclo[2.2.1]hept-3-ylcarboxylate (D21)

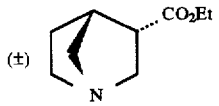

(D21)

(±) cis-2-benzyl-hexahydropyrano[3,4-c]pyrrole-4(1H)-one (D20) (180 g, 0.78 mole) in ethanol (400 ml) was stirred and cooled to 0° C. and hydrogen bromide gas introduced at such a rate that the temperature did not rise above 20° C. until the solution was saturated. The reaction was allowed to stand at room temperature for 6 h. The reaction was then poured into a well stirred mixture of chloroform (2 L) and saturated aqueous potassium carbonate solution (1.5 L) which was cooled by the addition of solid carbon dioxide. The organic layer was separated and the aqueous layer extracted with chloroform (4×1 L). The combined organic extracts were dried ($Na_2SO_4$) concentrated in vacuo to a gum. The gum was then stirred with ether (3×750ml) to remove any unreacted starting material and the ether insoluble gum dissolved in ethanol (1 L). Palladium on charcoal 10% (20 g) was then added and the mixture stirred under an atmosphere of hydrogen at 50° C. for 6 h when the uptake of hydrogen was complete. The reaction was then filtered through Kieselguhr and concentrated in vacuo to a gum. This was partitioned between chloroform and saturated aqueous potassium carbonate solution. The organic phase was separated, dried over sodium sulphate and concentrated in vacuo to a gum. Distillation in vacuo afforded the title compound (D21, 75 g, 0.44 mole, 56%) as an oil b.p. 90°–95° C.$_{0.5mmHg}$ $^1$H NMR ($CDCl_3$) δ: 1.28 (3H, t, J=8Hz), 1.3–1.45 (1H, m), 1.5–1.65 (1H, m), 2.5–2.7 (3H, m), 2.85–3.05 (5H, m), 4.15 (2H, q, J=8Hz)

$^{13}$C NMR $CDCl_3$ δ: 14.2 ($CH_3$), 25.3 (C-5), 40.9 and 46.3 (C-3 and C-4), 53.2, 55.7, 60.5, 61.2 (C-2, C-6, C-7, $CH_2O$), 173.2 (C=O)

DESCRIPTION 22

(±) exo- and endo-1-Azabicyclo[2.2.1]hept-3-ylcarbonyl chloride hydrochloride salt (D22)

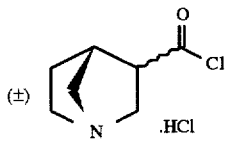

(D22)

(±) endo-Ethyl-1-azabicyclo[2.2.1]hept-3-yl carboxylate (D21) (4.0 g, 0.02 mole) in ethanol (20 ml) was added to a refluxing solution of sodium ethoxide prepared by adding sodium (0.4 g, 0.017 mole) to ethanol (80 ml). The mixture was heated under reflux for 4 h, cooled and evaporated to dryness to give a mixture of the exo and endo esters (D9) and (D21) in the ratio of 7:2. This was treated with hydrochloric acid (5N, 100 ml) and then thionyl chloride (50 ml) as in the method of Description 8 to yield a mixture of the title compounds (D22) as a yellow oil (4.7 g, 100%).

DESCRIPTION 23

(±)

endo-1-Azabicyclo[2.2.1]hept-3-yl-N-methoxycarboxamide (D23)

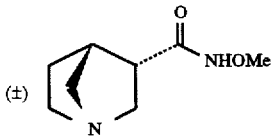

(D23)

(±) endo-Ethyl-1-azabicyclo[2.2.1]hept-3-yl carboxylate (D21) (3.0 g, 0.018 mole) was converted to the acid chloride hydrochloride salt and treated with methoxylamine hydrochloride (1.42 g, 0.017 mole) and pyridine as in the method of Description 8 to give the title compound (D23) (2.00 g, 66%) as a low melting solid.

$^1$H NMR ($CDCl_3$) δ: 1.40–1.65 (2H, m), 2.49–3.05 (9H, m), 3.77 (3H, s).

When a mixture of (±) exo and endo-1-azabicyclo[2.2.1] hept-3-ylcarbonyl chloride hydrochloride salt (D22, 4.76 g, 0.02 mole) was employed in the above reaction the product was a 7:2 mixture (3.15 g, 78%) of the exo and endo N-methoxycarboxamide (D10) and (D23).

DESCRIPTION 24

(±)

exo-1 -Azabicyclo[2.2.1]hept-3-yl-N-ethoxycarboxamide (D24)

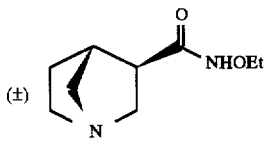

(D24)

(±) exo and endo-1-Azabicyclo[2.2.1]hept-3-ylcarbonyl chloride hydrochloride salt (D22) (4.66 g, 0.024 mole) was treated with ethoxylamine hydrochloride (2.4 g, 0.024 mole) and pyridine as in the method of Description 8 to give the title compound (D24) (2.0 g, 46%) as an oil. The endo isomer was not isolated.

$^1$H NMR ($CDCl_3$) δ: 1.05–1.22 (1H, m), 1.28 (3H, t, J=7Hz), 1.55–1.71 (1H, m), 2.28–3.12 (9H, m), 3.93 (2H, q, J =7Hz)

DESCRIPTION 25

(±) exo and endo-1-Azabicyclo[2.2.1]hept-3-yl-N-prop-2-ynyloxycarboxamide (D25)

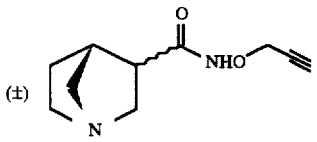

(D25)

(±) exo and endo-1-Azabicyclo[2.2.1]hept-3-ylcarbonylchloride hydrochloride salt (D22) (11.8 g, 0.06 mole) was treated with propargyloxylamine* hydrochloride (6.5 g, 0.06 mole) and pyridine as in the method of Description 8 to give the title compounds (D25) as a 7:2 mixture of exo and endo isomers (2.02 g, 16%).

*(U.S. Pat. No. 3,398,180; CA:57:728866)

DESCRIPTION 26

(±) endo-1-Azabicyclo[2.2.1]hept-3-ylcyclopropyl ketone (D26)

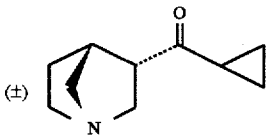

(D26)

(±) endo-Ethyl-1-azabicyclo[2.2.1]hept-3-ylcarboxylate (D21, 4 g, 23.7 mmole) was converted to the acid chloride hydrochloride salt as in the method of Description 2. To a mixture of this material (4.6 g, 23.7 mmole) and cyclopropyltrimethylsilane (1.92 g, 35 mmole) in dry dichloromethane (250 ml), under nitrogen, cooled in ice, was added aluminium chloride (7.89 g, 59 mmole) in portions. After refluxing for 17 h, the reaction mixture was cooled on ice, treated with saturated aqueous potassium carbonate (50 ml) and water (50 ml). The aqueous and organic phases were separated, and the aqueous phase extracted with chloroform (3×200 ml). The combined organic extracts were dried ($Na_2SO_4$) and evaporated to an oil which was chromatographed on silica gel in a gradient of 0–20% methanol in chloroform to afford the title compound (D26) as an oil (0.13 g, 3%).

DESCRIPTION 27

(±) exo- and endo-3-Oxo-3-(1-azabicyclo[2.2.1]hept-3-yl) propionitrile lithium salt (D27)

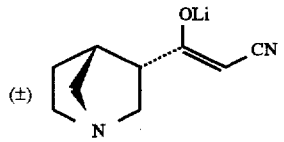

(D27)

A solution of diisopropylnmine (0.35 g, 5.92 mmole) in tetrahydrofuran (20 ml), under nitrogen, was cooled to −78° C. then treated with n-butyl lithium (3.7 ml of a 1.6M solution in hexane, 5.92 mmole) and N,N,N',N'- tetramethylethylenediamine (0.69 g, 5.92 mmole). The solution was allowed to warm up to −20° C. over about five minutes, then cooled back down to −78° C.

The solution was treated with acetonitrile (0.24 g, 5.92 mmole), then after fifteen minutes treated with (±) endo-ethyl-1-azabicyclo[2.2.1]hept-3-ylcarboxylate (D21, 0.5 g, 2.95 mmole) in tetrahydrofuran (2 ml). After 0.5 h the solution was concentrated in vacuo to afford the title compound (D27) as a beige solid (1.5 g) which was used without further purification.

EXAMPLE 1

(±)

1-Azabicyclo[2.2.2]oct-3-yl-N-methoxycarboximidoyl chloride oxalate salt (E1)

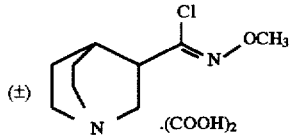

(E1)

(±) 1-Azabicyclo[2.2.2]oct-3-yl-N-methoxycarboxamide (D2, 2.77 g, 0.0151 mole) in nitromethane (50 ml) was treated with phosphorous pentachloride at −10° C. After 0.25 h the reaction mixture was poured into saturated aqueous potassium carbonate solution (30 ml) and extracted with chloroform (4×50 ml). The combined extracts were dried ($Na_2SO_4$) and evaporated to give an oil which was chromatographed on neutral alumina using 1% methanol/chloroform as eluant to yield the imidoyl chloride as a mobile oil (0.853 g, 28%).

$^1$H Nmr ($CDCl_3$) δ: 1.42 (1H, m), 1.68 (3H, m), 2.23 (1H, m), 2.63–2.96 (5H, m), 3.05 (1H, dt, J=10Hz, 1Hz), 3.35 (1H, dd, J=10Hz, 5Hz), 3.98 (3H, s).

$^{13}$C Nmr ($CDCl_3$) δ: 21.62, 25.03, 27.33, 44.69, 47.41, 47.49, 50.62, 63.10, 140.82.

Ir (film) 1660, 1040 $cm^{-1}$.

A portion of this material was converted to the oxalate salt which was recrystallised from methanol/acetone to give the title compound (E1) as a white crystalline solid, m.p. 143°–146° C.

$^1$H Nmr ($d_6$ DMSO) δ: 1.73 (2H, m), 1.92 (2H, m), 2.39 (1H, m), 3.08–3.30 (5H, m), 3.46 (2H, m), 3.94 (3H, s).

$^{13}$C Nmr ($d_6$ DMSO) δ: 18.26, 22 58, 23.27, 40.79, 45.14, 45.22, 47.19, 62.77, 137.95.

Analysis $C_9H_{15}N_2OCl.C_2H_2O_4$ requires C: 45.14; H: 5.85; N: 9.57; found C: 45.08; H: 5.84; N: 9.74

EXAMPLE 2

(±)

1-Azabicyclo2.2.2]oct-3-yl-N-methoxycarboximidic acid methyl ester oxidate salt (E2)

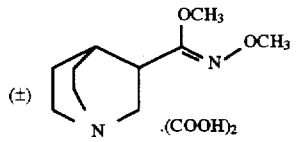

(E2)

(±) 1-Azabicyclo[2.2.2]oct-3-yl-N-methoxycarboximidoyl chloride (E1) (0.063 g, 0.0031 mole) in dry methanol (10 ml) was treated with sodium methoxide (0.0252 g, 0.0047 mole) at reflux for 48 h. The reaction mixture was concentrated in vacuo and the residue partitioned between saturated aqueous potassium carbonate solution (15 ml) and chloroform (5×50 ml). The combined organic extracts were dried ($Na_2SO_4$) and evaporated to an oil, which was chromatographed on neutral alumina using 2–20% methanol/chloroform to afford 3-cyano-1-azabicyclo[2.2.2]octane (0.097 g, 23%, spectral properties identical to D1) and the acid ester as a gum (0.129 g, 21%).

$^1$H Nmr ($CDCl_3$) δ: 1.52 ($^1$H, m), 1.77 (2H, m), 1.94 (1H, m), 2.12 (1H, m), 2.66 (1H, m), 2.85–3.15 (5H, m), 3.40 (1H, dd, J=10Hz, 5Hz), 3.78 (3H, s), 3.92 (3H, s).

$^{13}$C Nmr ($CDCl_3$) δ: 21.03, 24.27, 26 29, 37.10, 46.97, 47.19, 49.43, 58.70, 62.58, 155.48.

MS (CI) $M^+$+1–199.

A portion of this material was converted to the oxalate salt which was recrystallised from methanol/acetone to give the title compound (E2) as a white crystalline solid, m.p. 90°–93° C.

$^1$H Nmr ($d_6$ DMSO) δ: 1.61–1.93 (4H, m), 2.19 (1H, m), 3.00–3.23 (5H, m), 3.34 (2H, m), 3.68 (3H, s), 3.85 (3H, s).

$^{13}$C Nmr ($d_6$ DMSO) 4: 18.49, 22.61, 22.76, 34.13, 45.08, 45.38, 47.04, 57.87, 61.60, 154.18.

Analysis $C_{10}H_{18}N_2O_2.C_2H_2O_4$ requires C: 49.99; H: 6.99; N: 9.72; found C: 49.92; H: 7.09; N: 9.62

EXAMPLE 3

(±) α-(Methoxyimino)-α-(1-azabicyclo[2.2.2]oct-3-yl)acetonitrile hydrochloride salt (E3)

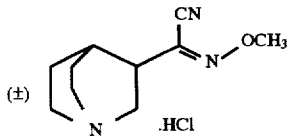

(E3)

(±) 1-Azabicyclo[2.2.2oct-3-yl-N-methoxycarboximidoyl chloride (E1) (0.067g, 0.33 mmol) in dry DMSO (5 ml) was treated with sodium cyanide (0.019 g, 0.40 mmol) at 100° C. for 5 h. The solvent was evaporated in vacuo and the residue partitioned between saturated aqueous potassium carbonate solution (10 ml) and chloroform (5×30 ml). The combined organic extracts were dried ($Na_2SO_4$) and evaporated to an oil, which was chromatographed on silica using 7% methanol/chloroform to afford 3-cyano-1-azabicyclo[2.2.2]octane (0.008 g, 19%, spectral properties identical to D1) and the imidoyl cyanide as crystallising oil (0.016 g, 27%).

$^1$H Nmr ($CDCl_3$) δ: 1.46 (1H, m), 1.56–1.77 (3H, m), 2.14 (1H, m), 2.62–3.00 (5H, m), 3.06 (1H, dt, J=10Hz, 1Hz), 3.27 (1H, dd, J=10Hz, 5Hz), 4.01 (3H, S).

$^{13}$C Nmr ($CDCl_3$) δ: 20.79, 25.01, 26.59, 39.22, 46.90, 47.00, 48.87,

A portion of this material was converted to the hydrochloride salt which was recrystallised from acetone/ether to give the title compound (E3) as a white crystalline solid, m.p. 176°–182° C.

$^1$H Nmr ($d_6$ DMSO) δ: 1.63–2.02 (4H, m), 2.32 (1H, m), 3.01–3.67 (7H, m), 4.07 (3H, s).

$^{13}$C Nmr ($D_6$ DMSO) δ: 18.1, 22.7, 23.3, 35.9, 44.9, 45.2, 46.2, 64.0, 109.9, 131.7

Analysis: $C_{10}H_{15}N_3O.HCl$ requires C: 52.29; H: 7.02; N: 18.29; found: C: 51.98; H: 7.10; N: 18.33

EXAMPLE 4

(±) 1-Azabicyclo[3.2.1]oct-5-yl ethynyl ketone

O-methyloxime oxalate salt (E4)

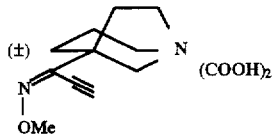

(E4)

Aqueous 12M sodium hydroxide (15 ml) at 0° C. was added to a mixture of 1-azabicyclo[3.2. ]oct-5-yl trimethylsilylethynyl ketone O-methyloxime (D7, 0.63 g, 0.0024 mole) and triethylbenzylamine bromide (0.22 g, 0.80 mole) in acetonitrile (15 ml) at 0° C. The reaction mixture was stirred at 0° C. for 10 minutes then diluted with ether (100 ml). The organic phase was separated, dried ($Na_2SO_4$), and evaporated. The residue was taken-up in dry ether (200 ml) and filtered through Kieselguhr, then evaporated to give the ethynyl oxime as a pale yellow oil. This material was converted to the oxalate and recrystallised from acetone to yield the title compound (E4) as a 6:1 mixture of cis and trans isomers (0.62 g, 93%) m.p. 119°–121° C.

Oxalate salt: $^1$H Nmr (major isomer, $d_6$ DMSO) δ: 1.65–2.25 (6H, m), 3.09–3.57 (6H, m), 3.86 (3H, s), 5.04 (1H, s)

$^{13}$C Nmr (major isomer, $d_6$-DMSO) 16.77, 31.04, 32.50, 46.86, 49.47, 51.33, 58.51, 62.34, 72.71, 93.45, 141.98

MS Calculated mass for $C_1H_6N_2O$=192.1263

Observed mass=192.1263

EXAMPLE 5

(±) 1-Azabicyclo[3.2.1]oct-5-yl-N-methoxycarboximidoyl chloride oxalate salt (E5)

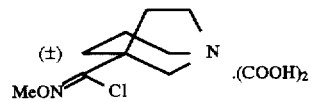

(E5)

Triphenylphosphine (2.20 g, 0.0084 mole) was added in a single portion to 1-azabicyclo[3.2.1]oct-5-yl-N-methoxycarboxamide (D8, 1.54 g, 0.0084 mole) and carbon tetrachloride (2 ml) in acetonitrile (50 ml) at reflux. After 2 minutes the reaction mixture was poured into saturated aqueous potassium carbonate solution (30 ml) and extracted with chloroform (4×50 ml). The combined extracts were dried ($Na_2SO_4$) and evaporated to give an oil which was chromatographed on silica using 10% methanol/chloroform as eluant to give the imidoyl chloride as a crystallising oil (0.84 g, 50%). A portion of this material was converted to the oxalate salt and recrystallised from methanol/acetone to give the title compound (E5) as colourless flakes m.p. 130°–132° C.

Oxalate: $^1$H Nmr ($d_6$ DMSO) δ: 1.72–2.29 (6H, m), 3.16–3.56 (6H, m), 3.90 (3H, s).

$^{13}$C Nmr ($d_6$ DMSO) δ: 16.68, 31.09, 32.44, 49.20, 49.34, 51.32, 58.58, 62.63, 139.74

Analysis: $C_9H_{15}N_2OCl.C_2H_2O_4$ requires C: 45.14; H: 5.85; N: 9.57; found C: 44.98; H: 5.76; N: 9.45

EXAMPLE 6

(±) α-(Methoxyimino)-α-(1-azabicyclo[3.2.1]oct-5-yl)

acetonitrile hydrochloride salt (E6)

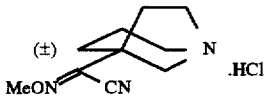

(E6)

(±) 1-Azabicyclo[3.2.1]oct-5-yl-N-methoxycarboximidoyl chloride (E5, 0.65 g, 0.0032 mole) was treated with sodium cyanide (0.23 g, 0.0047 mole) as in the method of Example 3 to give the cyano-oxime as an oil (0.41 g, 66%). A portion of this material was converted to the hydrochloride salt and recrystsllised from acetone/ether to give the title compound (E6) as a white crystalline solid m.p. 196°–198° C.

Hydrochloride: $^1$H Nmr ($d_6$ DMSO) δ: 1.76–2.33 (6H, m), 3.18–3.28 (2H, m), 3.33–3.56 (4H, m), 4.05 (3H, s).

$^{13}$C Nmr ($d_6$ DMSO) δ: 16.51, 30.37, 31.92, 45.70, 49.31, 50.94, 57.84, 64.06, 109.01, 133.57.

Analysis: $C_{10}H_{15}N_3O.HCl$ requires C: 52.29; H: 7.02; N: 18.29; found C: 52.10; H: 7.05; N: 18.04.

EXAMPLE 7

(±) 1-Azabicyclo[3.2. ]oct-5-yl-N-methoxycarboximidonyl bromide oxalate salt (E7)

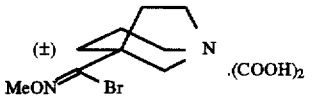

(E7)

Triphenylphosphine (0.86 g, 0.0033 mole) was added to a mixture of 1-azabicyclo[3.2.1]oct-5-yl-N-methoxycarboxamide (D8, 0.6 g, 0.0033 mole) and carbon tetrabromide (1.09 g, 0.0033 mole) in acetonitrile (30 ml) at reflux. The reaction mixture was refluxed for 4 h then poured into saturated potassium carbonate (30 ml) and extracted with chloroform (5×50 ml). The combined extracts were dried ($Na_2SO_4$) and evaporated to give an oil which was chromatographed on silica using 12% methanol/chloroform as eluant to afford the imidoyl bromide as an oil. This material was converted to the oxalate salt and recrystallised from acetone/ether to give the title compound (E7) as a white crystalline solid (0.15 g, 14%) m.p. 145°–147° C.

Oxalate salt: $^1$H Nmr ($d_6$ DMSO) δ: 1.72–2.26 (6H, m), 3.15–3.55 (6H, m), 3.93 (3H, s).

$^{13}$C Nmr ($d_6$ DMSO) δ: 16.74, 31.82, 33.14, 49.10, 50.39, 51.33, 58.94, 62.55, 133.70.

Analysis: $C_9H_{15}N_2OBr.Chdb\ 2H_2O_4$ requires C: 39.19; H: 5.08; N: 8.31; found C: 39.14; H: 5.13; N: 8.09

EXAMPLE 8

(±)

exo-1-Azabicyclo[2.2.1]hept-3-yl-N-methoxycarboximidoyl chloride oxalate salt (E8)

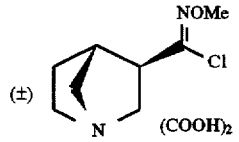

(E8)

exo-1-Azabicyclo[2.2.1]hept-3-yl-N-methoxycarboxamide (D10, 0.4 g, 0.0024 mole) was treated with triphenylphosphine (0.62 g, 0.0024 mole) and carbon tetrachloride (1 ml) in acetonitrile (30 ml) as in the method of Example 5 to give the imidoyl chloride as a colourless oil (0.15 g, 34%). A portion of this material was converted to the oxalate salt and recrystallised from acetone/methanol to yield the title compound (E8) as a white crystalline solid m.p. 118°–120° C.

Oxalate salt: $^1$H Nmr ($d_6$ DMSO) δ: 1.68 (1H, m), 1.98 (1H, m), 3.02–3.53 (8H, m), 3.91 (3H, s).

$^{13}$C Nmr ($d_6$ DMSO) δ: 26.73, 38.58, 39.81, 46.91, 51.43, 54.78, 56.54, 62.69, 137.73.

Analysis: $C_8H_{13}N_2OCl.C_2H_2O_4$ requires C: 43.10; H: 5.43; N: 10.05; found C: 42.98; H: 5.50; N: 9.74.

EXAMPLE 9

(±) exo-α-(Methoxyimino)-α-(1-azabicyclo[2.2.1]hept-3-yl)acetonitrile hydrochloride salt (E9)

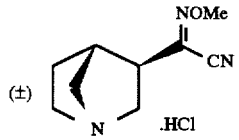

(E9)

(±) 1-Azabicyclo[2.2.1]hept-3-yl-N-methoxycarboximidoyl chloride (E8, 0.14 g, 0.0007 mole) was treated with sodium cyanide (0.06 g, 0.0012 mole) as in the method of Example 3 to give the cyano-oxime as a pale yellow oil (0.09 g, 68%). A portion of this material was converted to the hydrochloride salt and recrystallised from methanol/acetone to give the title compound (E9) as a white crystalline solid m.p. 213°–215° C.

Hydrochloride: $^1$H Nmr ($d_6$ DMSO) δ: 1.76 (1H,m), 2.04 (1H, m), 3.03–3.38 (5H, m), 3.52 (2H, m), 4.04 (3H, s).

$^{13}$C Nmr ($d_6$ DMSO) δ: 26.72, 39.67, 42.05, 51.50, 53.97, 56.55, 64.25, 110.44, 131.86

Analysis $C_9H_{13}N_3O.HCl$ requires C: 50.12; H: 6.54; N: 19.48; found C: 49.82; H: 6.60; N: 19.16.

EXAMPLE 10

(±)

1-Azabicyclo[2.2.2]oct-3-yl-N-methoxycarboximidoyl fluoride oxalate salt (E10)

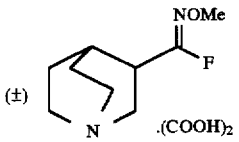

(E10)

A mixture of 1-azabicyclo[2.2.2]oct-3-yl-N-methoxycarboximidoyl chloride (E1, 0.1 g, 0.0005 mole) and cesium fluoride supported on calcium fluoride (5 g prepared by slowly evaporating to dryness a slurry of calcium fluoride in a solution of cesium flouride in methanol for 1 h at 80° C. under reduced pressure in a mole ratio of 5:1)* in DMF (15 ml) were neared at 145° C. for 5 days. The reaction mixture was filtered, concentrated in vacuo, and partitioned between saturated potassium carbonate and chloroform (4×50 ml). The combined organic extracts were dried ($Na_2SO_4$) and evaporated to give an oil which was chromatographed on silica gel using 10% methanol/chloroform as eluant to yield the imidoyl fluoride as an oil. Conversion to the oxalate salt afforded the title compound (E10) as a white crystalline solid (0.042 g, 31%)m.p. 102°–108° C.

*J. H. Clark, A. J. Hyde and D. K. Smith, J. Chem. Soc. Chem. Commun., 1986, 791.

Oxalate: $^1$H Nmr ($d_6$ DMSO) δ: 1.70–1.97 (5H, m), 3.10–3.37 (6H, m), 3.46 (1H, m), 3.79 (3H, s).

$^{13}$C Nmr ($d_6$DMSO) δ: 18.57, 21.99, 22.28, 33.62 (d, $^2J_{CF}$=28Hz), 45.08, 45.34, 46.09, 62.60, 151.40 (d, $^1J_{CF}$=329Hz).

M.S. Calculated mass for $C_9H_{15}N_2OF$=186.1168

Observed mass=186.1162

EXAMPLE 11

1-Azabicyclo[2.2.1]hept-4-yl-N-methoxycarboximidoyl chloride oxalate salt (E11)

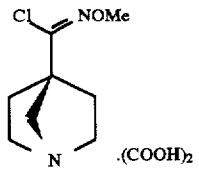

(E11)

1-Azabicyclo[2.2.1]hept-4-yl-N-methoxycarboxamide (D18, 2 g, 0.0118 mole) was treated with triphenylphosphine (3.09, 0.0118 mole) and carbon tetrachloride (4 ml) in acetonitrile (100 ml) as in the method of Example 5 to give the imidoyl chloride as a low-melting solid (1.70 g, 77%). A portion of this material was converted to the oxalate salt and recrystallised from methanol/acetone to give the title compound (E11) as a white crystalline solid m.p. 128°–130° C.

Oxalate salt: $^1$H Nmr ($d_6$DMSO) δ: 1.96 (2H, m), 2.20 (2H, m), 3.22–3.34 (4H, m), 3.45 (2H, m), 3.92 (3H, s).

$^{13}$C Nmr ($d_6$DMSO) δ: 31.59 (2C), 52.24 (2C), 52.73, 59.92, 62.72, 136.54.

Analysis $C_8H_{13}N_2OCl.C_2H_2O_4$ requires C: 43.10; H: 5.43; N: 10.05; found C: 43.06; H: 5.47; N: 10.04.

EXAMPLE 12

α-(Methoxyimino)-α-(1 -azabicyclo[2.2.1]hept-4-syl) acetonitrile hydrochloride salt (E12)

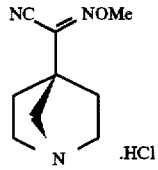

(E12)

1 -Azabicyclo[2.2.1 ]hept-4-yl-N-methoxycarboximidoyl chloride oxalate salt (E11, 0.4 g, 0.0021 mole) was treated with sodium cyanide (0.16 g, 0.0033 mole) as in the method of Example 3 to give the imidoyl cyanide as a crystallising oil. Conversion to the hydrochloride salt afforded the title compound (E12) as a white crystalline solid (0.20 g, 44%) m.p. 186°–187° C.

Hydrochloride: $^1$H Nmr ($d_6$DMSO) δ: 1.99 (2H, m) 2.24 (2H, m), 3.32–3.44 (4H, m), 3.53 (2H, m), 4.09 (3H, s).

$^{13}$C Nmr ($d_6$DMSO) δ: 30.66 (2C), 48.94, 51.89 (2C), 59.33, 64.16, 109.00, 130.10.

M.S. Calculated mass for $C_9H_{13}N_3O$=179.1059

Observed mass=179.1057

EXAMPLE 13

1-Azabicyclo[2.2.1]hept-4-yl-N-methoxycarboximidoyl bromide oxalate salt (E13)

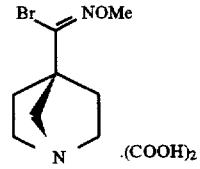

(E13)

1-Azabicyclo[2.2.1]hept-4-yl-N-methoxycarboxamide (D18, 0.7 g, 0.0041 mole) was converted to the hydrobromide salt and treated with triphenylphosphine (1.08 g, 0.004 mole) and carbon tetrabromide (1.37 g, 0.0041 mole) in acetonitrile (50 ml) at reflux for 1 h. The reaction mixture was poured into saturated potassium carbonate (30 ml) and extracted with chloroform (5×50 ml). The combined organic extracts were dried ($Na_2SO_4$) and evaporated to an oil which was chromatographed on silica using 2–3% methanol/chloroform as eluant to afford the imidoyl bromide as an oil (0.49 g, 51%). A portion of this material was converted to the oxalate salt and recrystallised from acetone/ether to give the title compound (E13) as colourless flakes m.p. 133°–134° C.

Oxalate salt: $^1$H Nmr ($d_6$ DMSO) δ: 1.96 (2H, m), 2.18 (2H, m), 3.22–3.36 (4H, m), 3.46 (2H, m), 3.94 (3H, s).

$^{13}$C Nmr ($d_6$DMSO) δ: 32.14 (2C), 52.17 (2C), 54.07, 60.35, 62.61, 129.66.

Analysis $C_8H_{13}N_2OBr.C_2H_2O_4$ requires C: 37.17; H: 4.68; N: 8.67; found C: 37.38; H: 4.67; N: 8.83

EXAMPLE 14

1-Azabicyclo[2.2.1]hept-4-yl-N-methoxycarboximidoyl fluoride oxalate salt (E14)

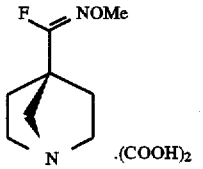

(E14)

1-Azabicyclo[2.2.1]hept-4-yl-N-methoxycarboxamide (D18, 1.6 g, 0.0094 mole) was converted to the hydrofluoride salt by the addition of hydrogen fluoride-pyridine (Aldrich). The salt was dissolved in refluxing acetonitrile (150 ml) and diethylaminosulphur trifluoride (DAST) (1.25 ml, 0.0095 mole) in acetonitrile (5 ml) was added in a single portion. The reaction mixture was immediately cooled and poured into saturated potassium carbonate (100 ml) and extracted with chloroform (4×100 ml). The combined organic extracts were dried ($Na_2SO_4$) and evaporated to an oil which was chromatographed on silica using 2–3% methanol/chloroform as eluant to yield the imidoyl fluoride as an oil (0.40 g, 25%). Addition of oxalic acid and recrystallisation from methanol/acetone gave the title compound (E14) as a white crystalline solid m.p. 114°–116° C.

Oxalate salt: $^1$H Nmr ($d_6$DMSO) δ: 1.89 (2H, m), 2.17 (2H, m), 3.16–3.29 (4H, m), 3.42 (2H, m), 3.77 (3H, s)

$^{13}$C Nmr ($d_6$ DMSO) δ: 29.86 (2C), 46.78 (d, $^2J_{CF}$= 29Hz), 52.08 (2C), 59.22, 62.66, 150.60 (d, $^1J_{CF}$=330Hz)

Analysis $C_8H_{13}N_2OF.C_2H_2O_4$ requires C: 45.80; H: 5.77; N: 10.68; found C: 45.79; H: 5.78; N: 10.72

EXAMPLE 15

(±) 1-Azabicyclo[2.2.2]oct-3-yl cyclopropyl ketone trans-O-methyloxime hydrochloride salt (E15)

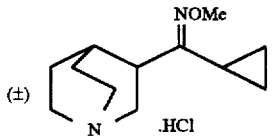

(E15)

(±) 1-Azabicyclo[2.2.2]oct-1-yl cyclopropyl ketone (D19, 0.1 g, 0.0006 mole) in methanol (15 ml) was treated with methoxylamine hydrochloride (0.15 g, 0.0018 mole) at reflux for 20 h. After cooling, the reaction mixture was concentrated in vacuo, saturated potassium carbonate (20 ml) was added and the mixture was extracted with chloroform (4×30 ml). The combined organic extracts were dried ($Na_2SO_4$) and evaporated to give an oil which was chromatographed on silica gel using 15–20% methanol/chloroform as eluant to afford the oxime as an oil (0.062 g, 53%). This was converted to the hydrochloride salt and recrystallised from methanol/acetone to give the title compound (E15) as a white crystalline solid m.p. 225°–228° C. (decomp.).

Hydrochloride: $^1$H Nmr ($d_6$ DMSO) δ: 0.66–0.89 (4H, m), 1.66 (1H, m), 1.80–2.06 (5H, m), 2.45 (1H, m), 3.03–3.25 (6H, m), 3.82 (3H, s).

$^{13}$C Nmr ($d_6$ DMSO) δ: 4.61, 5.16, 8.80, 17.89, 22.85, 23.52, 32.58, 44.95, 45.28, 47.34, 61.43, 157.66

M.S. Calculated mass for $C_{12}H_{20}N_2O$=208.1576

Observed mass=208.1576

EXAMPLE 16

(±) endo-1-Azabicyclo[2.2.1]hept-3-yl -N-methoxycarboximidoyl chloride oxalate salt (E16)

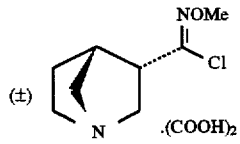

(E16)

(±) endo-1-Azabicyclo[2.2.1]hept-3-yl-N-methoxycarboxamide (D23) (1.42 g, 0.0083 mole) was treated with triphenylphosphine (2.19 g, 0.0083 mole) and carbon tetrachloride (2 ml) in acetonitrile (50 ml) as in the method of Example 5 to give the imidoyl chloride as a colourless oil (0.6 g, 38%). A portion of this material was converted to the oxalate salt and crystallised from ethanol/diethyl ether to yield the title compound (E16) as a white crystalline solid m.p. 123°–125° C.

Oxalate salt: $^1$H NMR ($d_6$ DMSO) δ: 1.55–1.68 (1H, m), 1.95–2.05 (1H, m), 3.10–3.70 (8H, m), 4.01 (3H, s).

$^{13}$C NMR ($d_6$ DMSO) δ: 22.13, 39.27, 45.61, 51.91, 52.59, 58.47, 62.78, 136.78

Analysis: $C_8H_{13}N_2OCl.C_2H_2O_4$ requires C: 43.10; H: 5.43; N: 10.05; found C: 42.99; H: 5.47; N: 9.86

EXAMPLE 17

(±) endo-α-(Methoxyimino)-α-(1-azabicyclo[2.2.1]hept-3-yl)acetonitrile oxalate salt (E17)

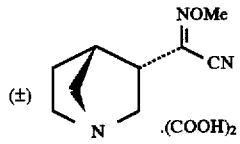

(E17)

(±) endo-1-Azabicyclo[2.2.1]hept-3-yl-N-methoxycarboximidoyl chloride (E16) (0.5 g, 0.0027 mole) was treated with sodium cyanide (0.2 g, 0.004 mole) as in the method of Example 3 to give the cyano-oxime as an oil (0.035 g, 7%). This material was converted to the oxalate salt and crystallised from ethanol/diethyl ether to give the title compound (E17) as a white crystalline solid m.p. 125°–130° C.

Oxalate salt: $^1$H NMR ($d_6$ DMSO) δ: 1.59–1.72 (1H, m), 1.97–2.11 (1H, m), 3.11–3.73 (8H, m), 4.17 (3H, s)

$^{13}$C NMR ($d_6$ DMSO) δ: 22.05, 39.06, 40.88, 52.03, 52.18, 58.93, 64.05, 110.10, 130.36

M.S. Calculated mass for $C_9H_{13}N_3O$=179.1058

Observed mass=179.1062

EXAMPLES 18 AND 19

(±) exo- and endo-1-Azabicyclo[2.2.1]hept-3-yl-N-methoxycarboximidoyl bromide oxalate salts (E18) and (E19)

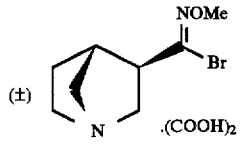

(E18)

-continued

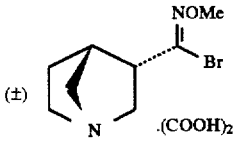

(E19)

A 7:2 mixture of (±) exo- and endo-1-azabicyclo[2.2.1] hept-3-yl-N-methoxycarboxamide (D10) and (D23) (1.5 g, 0.0088 mole) was converted to the hydrobromide salts by addition of one equivalent of HBr in acetone. The mixture was evaporated to dryness and the residue dissolved in refluxing acetonitrile (50 ml). Carbon tetrabromide (2.9 g, 0.0088 mole) was added followed by triphenylphosphine (2.3 g, 0.0088 mole). The mixture was heated under reflux for 30 min. A further amount of carbon tetrabromide (1.0 g, 0.003 mole) and triphenylphosphine (0.8 g, 0.003 mole) was added to drive the reaction to completion followed by a further 30 min at reflux. The mixture was allowed to cool slightly and saturated potassium carbonate solution (50 ml) was added with vigorous stirring. The mixture was extracted with chloroform (3×100 ml) and the combined organic extracts were washed with 2N hydrochloric acid (2×100 ml). The combined acid extracts were then saturated by careful addition of potassium carbonate. The oil which separated was extracted into chloroform (2×100 ml) which was dried ($Na_2SO_4$), filtered and evaporated to dryness.

The residue was chromatographed on silica gel eluting with 0–5% methanol/chloroform. This gave the exo compound as the less polar fraction (0.37 g, 18%) which was converted to the oxalate salt. Trituration with diethyl ether gave the title compound (E18) (0.47 g) as a white crystalline solid m.p. 98°–102° C.

The more polar fraction gave the endo isomer (0.07 g, 4%) which was converted to the oxalate salt. Crystallisation from ethanol/diethyl ether gave the title compound (E19) (0.068 g) as a white crystalline solid m.p. 144°–148° C.

(E18) Oxalate salt $^1$H NMR ($d_6$DMSO) δ: 1.72–1.83 (1H, m), 2.01–2.15 (1H, m), 3.12–3.62 (8, m), 4.02 (3H, s).

$^{13}$C NMR ($d_6$ DMSO) δ: 26.94, 40.39, 49.45, 51.70, 55.56, 56.70, 62.92, 131.27

Analysis: $C_8H_{13}N_2OBr.C_2H_2O_4$ requires C: 37.17; H: 4.68; N: 8.67; found C: 37.14; H: 4.64; N: 8.66

(E19) Oxalate salt $^1$H NMR ($d_6$ DMSO) δ: 1.55–1.70 (1H, m), 1.91–2.07 (1H, m), 3.09–3.73 (8H, m), 4.04 (3H, s)

$^{13}$C NMR ($d_6$ DMSO) δ: 22.03, 40.12, 47.64, 51.91, 52.96, 58.20, 62.68, 129.87

Analysis: $C_8H_{13}N_2OBr.C_2H_2O_4$ requires C: 37.17; H: 4.68; N: 8.67; found C: 37.31; H: 4.67; N: 8.60

EXAMPLE 20

(±) exo-1-Azabicyclo[2.2.1]hept-3-yl-N-methoxy carboximidoyl fluoride oxalate salt (E20)

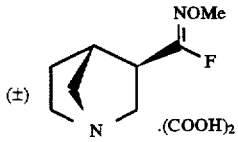

(E20)

(±) exo-1-Azabicyclo[2.2.1]hept-3-yl-N-methoxycarboximidoyl bromide (E18) (0.14 g, 0.0006 mole) in dry dimethylformamide (10ml) was heated at 140° C. for 20 h with cesium fluoride supported on calcium fluoride (6.0 g)*. The mixture was allowed to cool and then filtered washing the filter cake with dimethylformamide (10 ml). The filtrate was evaporated to dryness and the residue chromatographed on silica eluting with 0–5% methanol/chloroform. This gave the fluoro compound as an oil (0.025 g, 24%). This material was converted to the oxalate and crystallised from ethanol/diethyl ether to yield the title compound (E20) as a white crystalline solid m.p. 115°–117° C.

* J. Chem. Soc., Chem. Commun., 791 (1986)

Oxalate salt $^1$H NMR ($d_6$ DMSO) δ: 1.59–1.83 (1H, m), 1.88–2.03 (1H, m), 2.95–3.41 (8H, m), 3.77 (3H, s).

M.S. Calculated mass for $C_8H_{12}N_2OF$=172.1012
Observed mass=172.1012

EXAMPLE 21

(±) exo-1-Azabicyclo[2.2.1]hept-3-yl-N-ethoxy carboximidoyl chloride oxalate salt (E21)

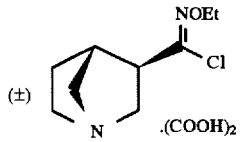

(E21)

(±) exo-1-Azabicyclo[2.2.1]hept-3-yl-N-ethoxycarboxamide (D24) (0.5 g, 0.0027 mole) was treated with triphenylphosphine (0.72 g, 0.0027 mole) and carbon tetrachloride (1 ml) in acetonitrile (20 ml) as in the method of Example 5 to give the imidoyl chloride as a colourless oil (0.15 g, 27%). This material was converted to the oxalate and crystallised from ethanol/diethyl ether to give the title compound (E21) as a white crystalline solid m.p. 126°–128° C.

Oxalate salt $^1$H NMR ($d_6$ DMSO) δ: 1.34 (3H, t, J=7Hz)), 1.70–1.83 (1H, m), 2.00–2.15 (1H, m), 3.11–3.64 (8H, m), 4.27 (2H, q, J=7Hz).

$^{13}$C NMR ($d_6$ DMSO) δ: 14.27, 26.68, 39.65, 47.03, 51.40, 54.77, 56.51, 70.41, 137.31

Analysis: $C_9H_{15}N_2OCl.C_2H_2O_4$ requires C: 45.14; H: 5.85; N: 9.57: found C: 44.90: H: 5.80: N: 9.34

EXAMPLE 22

(±) exo-α-(Ethoxyimino)-α-(1-azabicyclo[2.2. 1] hept-3-yl)acetonitrile oxalate salt (E22)

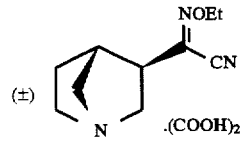

(E22)

(±) exo-1-Azabicyclo[2.2.1]hept-3-yl-N-ethoxycarboximidoyl chloride (E21) (0.415 g, 0.002 mole) was treated with sodium cyanide (0.16 g, 0.003 mole) as in the method of Example 3 to give the cyano-oxime as an oil (0.2 g, 51%). This material was converted to the oxalate salt sad crystallised from acetone/diethyl ether to give the title compound (E22) as a white crystalline solid m.p. 110°–112° C.

Oxalate salt $^1$H NMR ($d_6$ DMSO) δ: 1.37 (3H, t, J=7Hz), 1.72–1.85 (1H, m), 2.01–2.15 (1H, m), 3.05–3.65 (8H, m), 4.40 (2H, q, J=7Hz).

$^{13}C$ NMR ($d_6$ DMSO) δ: 14.19, 26.83, 39.62, 42.14, 51.46, 54.23, 56.39, 71.92, 110.32, 131.58

Analysis: $C_{10}H_{15}N_3O.C_2H_2O_4$ requires C: 50.88; H: 6.05; N: 14.83; found C: 50.70; H: 6.04; N: 14.61

EXAMPLE 23

(±) exo-1-Azabicyclo[2.2.1]hept-3-yl-N-ethoxy carboximidoyl bromide oxalate salt (E23)

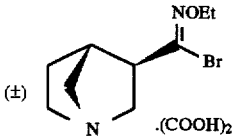

(E23)

(±) 1-Azabicyclo[2.2.1]hept-3-yl-N-ethoxycarboxamide (D24) (2.72 g, 0.0147 mole) was converted to the hydrobromide salt and treated with carbon tetrabromide (6.3 g, 0.19 mole) and triphenylphosphine (5.0 g, 0.019 mole) as in the method of Example 13 to give the imidoyl bromide as an oil (0.338 g, 9%). A portion of this material was converted to the oxalate salt and crystallised from ethanol/diethyl ether to give the title compound (E23) as a white crystalline solid m.p. 138°–140° C.

Oxalate salt: $^1H$ NMR ($d_6$ DMSO) δ: 1.33 (3H, t, J=7Hz), 1.71–1.85 (1H, m), 2.00–2.17 (1H, m), 3.12–3.61 (8H, m), 4.30 (2H, q, J=7Hz)

$^{13}C$ NMR ($d_6$ DMSO) δ: 14.33, 26.64, 40.12, 49.32, 51.48, 55.41, 56.47, 70.35, 130.56

M.S. calculated mass for $C_9H_{15}N_2O^{79}Br$=246.0366

Observed mass=246.0363

Calculated mass for $C_9H_{15}N_2O^{81}Br$=248.0345

Observed mass=248.0348

EXAMPLES 24 AND 25

(±) exo- and endo-1-Azabicyclo[2.2.1]hept-3-yl-N-prop-2-ynyloxycarboximidoyl chloride oxalate salts (E24) and (E25)

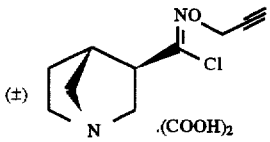

(E24)

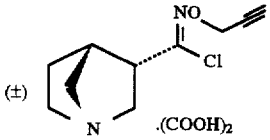

(E25)

(±) exo- and endo-1-Azabicyolo[2.2.1]hept-3-yl-N-prop-2-ynloxycarboxamide (D25) (1.0 g, 0.0051 mole) was treated with triphenylphospine (1.35 g, 0.0051 mole) and carbon tetrachloride (2.0 ml) in acetonitrile as in the method of Example 5. This gave the imidoyl chlorides which were separated by chromatography on silica eluting with 0–5% methanol/chloroform. This gave the exo compound as the less polar fraction (0.108 g, 10%) which was converted to the oxalate salt. Crystallisation from ethanol/diethyl ether gave the title compound (E24) (0.12 g) m.p. 103°–105° C.

The more polar fraction gave the endo isomer (0.046 g, 4%) which was converted to the oxalate salt. Crystallisation from ethanol/diethyl ether gave the title compound (E25) (0.055 g) m.p. 150°–156° C.

(E24) Oxalate salt $^1H$ NMR ($d_6$ DMSO) δ: 1.71–1.86 (1H, m), 2.01–2.15 (1H, m), 3.09–3.61 (8H, m), 3.69–3.74 (1H, m), 4.90 (2H, s).

$^{13}C$ NMR ($d_6$DMSO) δ: 26.68, 39.73, 47.09, 51.46, 54.80, 56.50, 62.40, 78.71, 79.12, 139.46

Analysis: $C_{10}H_{13}N_2OCl.C_2H_2O_4$ requires C: 47.61; H: 4.99; N: 9.25; found C: 47.63; H: 5.00; N: 9.05

(E25) Oxalate Salt $^1H$ NMR ($d_6$DMSO) δ: 1.57–1.70 (1H, m), 1.95–2.04 (1H, m), 3.04–3.68 (8H, m), 3.68–3.72 (1H, m), 4.92 (2H, s).

$^{13}C$ NMR ($d_6$DMSO) δ: 22.22, 39.31, 45.80, 51.86, 52.76, 58.54, 62.45, 78.62, 79.20, 138.61

Analysis: $C_{10}H_{13}N_2OCl.C_2H_2O_4$ requires C: 47.61; H: 4.99; N: 9.25; found C: 47.26; H: 4.92; N: 8.95

EXAMPLE 26

(±) exo-1-Azabicyclo[2.2.1]hept-3-yl cyclopropyl ketone O-methyloxime oxalate salt (E26)

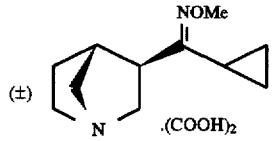

(E26)

A solution of (±) endo-1-azabicyclo[2.2.1]hept-3-yl cyclopropyl ketone (D26) (0.13 g, 1.6 mmole) in dry methanol (7 ml), under nitrogen, was treated with methoxylamine hydrochloride (0.13 g, 3.2 mmole) then tefluxed for 41 h. Additions of further methoxylamine hydrochloride (0.39 g, 9.6 mmole) and pyridine (0.186 g, 4.8 mmole) were made during this period. The reaction was concentrated in vacuo, treated with saturated aqueous potassium carbonate (10 ml) then extracted with chloroform (4×30 ml). The combined organic extracts were dried ($Na_2SO_4$), concentrated in vacuo and the residue chromatographed on silica eluting with 10% methanol in chloroform to afford the oxime ether as a clear gum (19 mg, 25%). This was converted to the oxalate salt which was recrystallised from methanol/ether to give the title compound (E26) as a white solid m.p. 124° C. (decomp).

$^1H$ NMR ($CDCl_3$) (free base) δ: 0.58–0.75 (2H, m), 0.79–0.95 (2H, m), 1.19–1.32 (2H, m), 1.63–1.82 (2H, m), 2.41–2.50 (1H, m), 2.58–2.77 (4H, m), 2.95–3.15 (2H, m), 3.86 (3H, s).

M.S. Calculated mass for $C_{11}H_{18}N_2O$=194.1419

Observed mass=194.1428

EXAMPLE 27 AND 28

(±) exo- and endo-3-Oxo-3-(1-azabicyclo[2.2.1] hept-3-yl)propionitrile-O-methyl oxime oxalate salts (E27) and (E28)

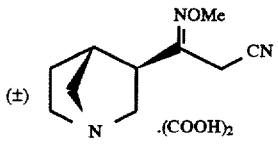

(E27)

-continued

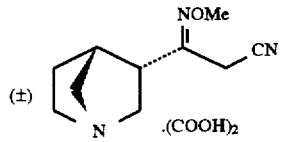

(E28)

A solution of (±) exo- and endo-3-oxo-3-(1-azabicy-clo [2.2.1]hept-3-yl)propionitrile lithium salt (D27) (1.5 g, approximately 2.95 mmoles) in dry methanol (15 ml), under nitrogen, was cooled to 0° C. then treated with methoxylamine hydrochloride (0.49 g, 5.9 mmole) and acetic acid (0.18 g, 0.295 mmole). The reaction was allowed to warm to room temperature over 17 h then heated at reflux for 1 h. The reaction mixture was concentrated in vacuo, treated with saturated aqueous potassium carbonate (20 ml) then extracted with chloroform (20 ml×4). The combined organic extracts were dried ($Na_2SO_4$) then concentrated in vacuo and the residue chromatographed on silica in a gradient of 0–5% methanol in chloroform. This afforded the exo-oxime (85 mg, 15%) and endo-oxime (19 mg, 3%) as gums.

The endo-isomer was converted to the oxalate salt and recrystallised from methanol/ether to give the title compound (E28) as a white solid m.p. 127° C. (decomp).

The exo-isomer was converted to the oxalate salt and recrystallised from acetone/ether to give the title compound (E27) as a hygroscopic solid.

(E28) Free base $^1$H NMR ($CDCl_3$) δ: 1.26–1.38 (1H, m), 1.47–1.63 (1H, m), 2.55–2.70 (2H, m), 2.76–3.18 (6H, m), 3.35 (2H, ABq), 3.87 (3H, s).

M.S. Calculated mass for $C_{10}H_{15}N_3O$=193.1215

Observed mass=193.1212

(E27) Oxalate salt $^1$H NMR ($d_6$DMSO) δ: 1.5–1.76 (1H, m), 1.94–2.12 (1H, m), 2.87–3.42 (8H, m), 3.74 (2H, ABq), 3.87 (3H, s)

$^{13}$C NMR ($d_6$DMSO) δ: 17.65, 26.92, 38.88, 43.96, 51.47, 53.31, 55.88; 62.14, 110.62, 148.24

M.S. Calculated mass for $C_{10}H_{15}N_3O$=192.1215

Observed mass=193.1215

EXAMPLES 29 AND 30

(−) α-(Methoxyimino)-α-(1 -azabicyclo[2.2.2]oct-3-yl)-acetonitrile oxalate salt (E29) and (+)

α-(methoxyimino)-α-(1-azabicyclo[2.2.2]oct-3-yl) acetonitrile oxalate salt (E30)

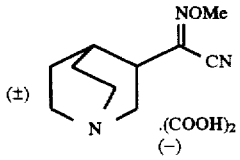

(E29)

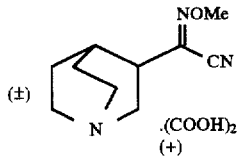

(E30)

A solution of (±) α-(methoxyimino)-α-(1-azabicyclo [2.2.2]oct-3-yl)acetonitrile (E3) (0.3 g, 1.55 mmol) in methanol (10 ml) was treated with (S)-(+)-1,1'-binaphthyl-2,2'-diyl hydrogen phosphate (0.38 g, 1.09 mmol) and the resulting solution concentrated in vacuo to leave a colourless oil. This material was dissolved in hot acetone (15 ml), diluted with ether (5 ml) and left to stand at room temperature for 24 h. The white crystalline solid was filtered off (372 mg) and recrystallised a further three times from methanol/acetone to give 260 mg of white solid. This material was treated with saturated potassium carbonate (50 ml) and extracted with chloroform (3×50 ml). The combined extracts were dried ($Na_2SO_4$) and concentrated in vacuo to give a colourless oil (90 mg), which was converted to its oxalate salt and recrystallised from methanol/acetone to give the title compound (E29) as a white solid m.p. 151°–153° C.

Oxalate salt: $[\alpha]^{20}_D$=−13.4° (C=0.932% in ethanol).

The purity of the enantiomer was confmned as >95% by chiral HPLC [2×(chiral - AGP, 100×4.0 mm) coupled in series to make a total column length of 200 mm using 0.02M of phosphate (pH 7.0) as eluant].

The mother liquors from the above recrystallisations were combined, concentrated in vacuo and the residue partitioned between saturated potassium carbonate (50 ml) and chloroform (3×50 ml). The combined extracts were dried ($Na_2SO_4$) and concentrated in vacuo to leave a colourless oil (188 mg), which was dissolved in methanol (10 ml) and treated with (R)-(−)-1,1'-binaphthyl-2,2'- diyl hydrogen phosphate (0.27 g, 0.78 mmol). The resulting solution was concentrated in vacuo to give a colourless oil which was taken-up in hot acetone (15 ml), treated with ether (5 ml) and left to stand at room temperature for 24 h. The white crystalline solid was filtered off (416 mg) and recrystallised twice from methanol/acetone to give 297 mg of a white solid. This material was treated with saturated potassium carbonate (50 ml) and extracted with chloroform (3×50 ml). The combined organic extracts were dried ($Na_2SO_4$) and concentrated in vacuo to give a colourless oil (94 mg), which was converted to the oxalate salt and recrystallised from methanol/acetone to give the title compound (E30) as a white solid m.p. 154°–156° C.

Oxalate salt: $[\alpha]^{20}_D$=−14.4° (C=0.424% in ethanol)

EXAMPLE 31

(±)

1-Azabicyclo[3.2.1]oct-5-yl-N-methoxycarboximidoyl fluoride oxalate salt (E31)

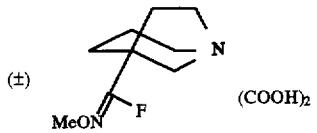

(E31)

Pyridine (3 ml, 0.037 mole) was added to a solution of (±) 1-azabicyclo[3 2.1]oct-5-yl-N-methoxycarboxamide (D8, 5.4 g, 0.029 mole) in acetone (100 ml). The solution was then made just acidic by the addition of hydrogen fluoride-pyridine (Aldrich) and evaporated in vacuo. The resultant gum was co-evaporated with toluene, dried under vacuum and then taken-up in refluxing dry acetonitrile (300 ml). Diethylaminosulphur trifluoride (DAST) (4.26 ml, 0.032 mole) in acetonitrile (20 ml) was added in a single portion and the reaction mixture was immediately cooled and poured into saturated potassium carbonate (150 ml). The mixture was extracted with chloroform (3×200 ml) and the combined extracts were dried ($Na_2SO_4$) and evaporated to an oil. Chromatography on silica using 4% methanol/chloroform as eluant afforded the imidoyl fluoride as a yellow oil (1.62 g, 31%). Addition of oxalic acid and recrystallisation from methanol/acetone gave the title compound (E31) as a white crystalline solid m.p. 104°–107° C.

Oxalate salt: $^1$H NMR ($d_6$ DMSO) δ: 1.70–2.30 (6H, m), 3.10–3.55 (6H, m), 3.76 (3H, s).

$^{13}$C NMR ($D_6$ DMSO) δ: 16.31, 29.78, 30.52, 43.82 (d, $^2J_{CF}$=27Hz), 49.55, 51.33, 57.63, 62.50, 152.36 (d, $^1J_{CF}$=333Hz).

Analysis $C_9H_{15}N_2OF.C_2H_2O_4$ requires C: 47.82; H: 6.2; N: 10.14; found C: 47.74; H: 6.15; N: 10.09

BIOLOGICAL ACTIVITY

Radio ligand Binding

Cerebral cortex from Hooded Lister rats (Olac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H-OXO-M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 3H-QNB (Amersham International). For 3H-OXO-M, 1 ml of membranes is diluted to 6 ml and 0.1 ml mixed with test compound and 2 nM (c. 250,000 cpm) 3H-OXO-M (New England Nuclear).

Non-specific binding of 3H-QNB is defined using 1 μM Atropine sulphate (2 μM Atropine) and of 3H-OXO-M using 10 μM Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as $IC_{50}$ values (i.e. the concentration which inhibits binding of the ligand by 50%) for the displacement of the muscarinic agonist 3H-OXO-M and the muscarinic antagonist 3H-QNB. The ratio $IC_{50}$(3H-QNB)/$IC_{50}$(3H-OXO-M) gives an indication of the agonist character of the compound. Agonists typically exhibit a large ratio; antagonists typically exhibit a ratio near to unity. The results are shown in Table 1.

TABLE 1

| Compound | [3H]-OXO-M $IC_{50}$ (nM) | [3H]-QNB $IC_{50}$ (nM) |
|---|---|---|
| E1 | 93 | 897 |
| E2 | 1000 | 8000 |
| E3 | 29 | 493 |
| E4 | 162 | 1458 |
| E5 | 72 | 3816 |
| E6 | 114 | 251 |

TABLE 1-continued

| Compound | [3H]-OXO-M $IC_{50}$ (nM) | [3H]-QNB $IC_{50}$ (nM) |
|---|---|---|
| E7 | 190 | 2850 |
| E8 | 64 | 3328 |
| E9 | 25 | 2100 |
| E10 | 34 | 2108 |
| E11 | 38 | 9000 |
| E12 | 21 | 1995 |
| E13 | 170 | 10030 |
| E14 | 48 | 15504 |
| E15 | 386 | 22237 |
| E16 | 99 | 7000 |
| E17 | 16 | 3600 |
| E18 | 46 | 11000 |
| E19 | 127 | 3600 |
| E20 | 11 | 3000 |
| E21 | 570 | 15500 |
| E22 | 233 | 10000 |
| E24 | 112 | 2100 |
| E27 | 71 | 1100 |
| E28 | 750 | 16500 |
| E29 | 180 | 1800 |
| E30 | 20 | 340 |

We claim:

1. A compound of formula (I) or a pharmaceutically acceptable salt thereof:

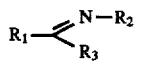

(I)

wherein $R_1$ represents

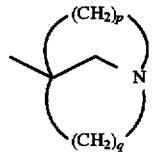

(A)

or

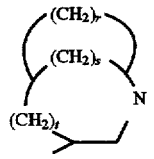

(B)

in which each of p and q independently represents an integer of 2 to 4, r represents an integer of 2 to 4, s represents 1 or 2 and t represents 0 or 1;

$R_2$ is a group $OR_4$ where $R_4$ is $C_{1-4}$ alkyl, $C_{2-4}$ alkenyl, $C_{2-4}$ alkynyl, a group $OCOR_5$ where $R_5$ is hydrogen or $R_4$, or a group $NHR_6$ or $NR_7R_8$ where $R_6$, $R_7$ and $R_8$ are independently $C_{1-2}$ alkyl; and $R_3$ is chloro, fluoro, bromo, $C_{1-3}$ alkyl substituted by one, two or three halogen atoms, —CN, [—$CN_2CN$], $CH_2CN$, —$SCH_3$, or —O—$CH_3$.

2. A compound according to claim 1, in which p represents 2 and q represents 2 or 3, or the combination (r,s,t) takes the value (2,2,0), (2,1,1), (3,1,1), (2,1,0) or (3,1,0).

3. A compound according to claim 1, in which $R_2$ is methoxy, ethoxy, allyloxy, propargyloxy, acetoxy or dimethylamino.

4. A compound according to claim 1, in which $R_3$ is chloro, fluoro, bromo, CN, $OCH_3$, or —$CH_2CN$.

5. (±) 1-Azabicyclo[2.2.2]oct-3-yl-N-methoxycarboximidoyl chloride, (±) 1-azabicyclo[2.2.2]oct-3-yl-N-methoxycarboximidic acid methyl ester, (±) α-(methoxyimino)-α-(1-azabicyclo[2.2.2]oct-3-yl) acetonitrile, (±) 1-azabicyclo[3.2.1]oct-5-yl-N-methoxycarboximidoyl chloride, (±) α-(methoxyimino)-α-(1-azabicyclo[3.2.1]oct-5-yl) acetonitrile, (±) 1-azabicyclo[3.2.1]oct-5-yl-N-methoxycarboximidoyl bromide, (±) exo-1-azabicyclo[2,2,1]hept-3-yl-N-methoxycarboximidoyl chloride, (±) exo-α-(methoxyimino)-α-(1-azabicyclo[2,2,1]hept-3-yl)acetonitrile, (±) 1-azabicyclo[2.2.2]oct-3-yl-N-methoxycarboximidoyl fluoride, 1-azabicyclo[2,2,1]hept-5-yl-N-methoxycarboximidoyl chloride, α-(methoxyimino)-α-(1-azabicyclo[2,2,1]hept-4-yl) acetonitrile, 1-azabicyclo[2,2,1]hept-4-yl-N-methoxycarboximidoyl bromide, 1-azabicyclo[2,2,1]hept-4-yl-N-methoxycarboximidoyl fluoride, (±) endo-1-azabicyclo[2,2,1]hept-3-yl-N-methoxycarboximidoyl chloride, (±) endo-α-(methoxyimino)-α-(1-azabicyclo[2,2,1]hept-3-yl)acetonitrile, (±) exo-1-azabicyclo[2,2,1]hept-3-yl-N-methoxycarboximidoyl bromide, (±) endo-1-azabicyclo[2,2,1]hept-3-yl-N-methoxycarboximidoyl bromide, (±) exo-1-azabicyclo[2,2,1]hept-3-yl-N-methoxycarboximidoyl fluoride, (±) exo-1-azabicyclo[2,2,1]hept-3-yl-N-ethoxycarboximidoyl chloride, (±) exo-α-(ethoxyimino)-α-(1-azabicyclo[2,2,1]hept-3-yl) acetonitrile, (±) exo-1-azabicyclo[2,2,1]hept-3-yl-N-ethoxycarboximidoyl bromide, (±) exo-1-azabicyclo[2,2,1]hept-3-yl-N-prop-2-ynyloxy-carboximidoyl chloride, (±) endo-1-azabicyclo[2,2,1]hept-3-yl-N-prop-2-ynyloxy-carboximidoyl chloride, (±) exo-3-oxo-3-(1-azabicyclo[2,2,1]hept-3-yl) propionitrile-O-methyl oxime, (±) endo-3-oxo-3-(1-azabicyclo[2,2,1]hept-3-yl) propionitrile-O-methyl oxime, (−) α-(methoxyimino)-α-(1-azabicyclo[2.2.2]oct-3-yl) acetonitrile, (+) α-(methoxyimino)-α-(1-azabicyclo[2.2.2]oct-3-yl) acetonitrile or (±) 1-azabicyclo[3.2.1]oct-5-yl-N-methoxycarboximidoyl fluoride, or a pharmaceutically acceptable salt of any of the foregoing compounds.

6. A compound of formula (IIa):

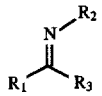

(IIa)

wherein $R_2'$ represents hydroxy and $R_1$ and $R_3$ are as defined in claim 1 *with the proviso that $R_3$ is not Br.*

7. A pharmaceutical composition which comprises an effective amount of a compound according to claim 1 and a pharmaceutically acceptable carrier.

8. A method of treatment or prophylaxis of dementia in mammals, which comprises administering to the sufferer an effective amount of a compound according to claim 1.

*9.* (−) α-(*Methoxyimino*)-α-(*1-azabicyclo*[*2.2.2*]*oct-3-yl*) *acetonitrile or a pharmaceutically acceptable salt thereof.*

*10.* (+) α-(*Methoxyimino*)-α-(*1-azabicyclo*[*2.2.2*]*oct-3-yl*)*acetonitrile or a pharmaceutically acceptable salt thereof.*

*11. A pharmaceutical composition comprising an effective amount of a compound defined by claim 9 and a pharmaceutically acceptable carrier therefor.*

*12. A pharmaceutical composition comprising an effective amount of a compound defined by claim 10 and a pharmaceutically acceptable carrier therefor.*

*13. A method of treatment or prophylaxis of dementia in mammals comprising administering to said mammal an effective amount of a compound defined by claim 9.*

*14. A method of treatment or prophylaxis of dementia in mammals comprising administering to said mammal an effective amount of a compound defined by claim 10.*

* * * * *